(12) United States Patent
Lee et al.

(10) Patent No.: US 12,409,304 B2
(45) Date of Patent: Sep. 9, 2025

(54) DRUG DELIVERY DEVICES WITH DRUG-PERMEABLE COMPONENT AND METHODS

(71) Applicant: TARIS Biomedical LLC, Lexington, MA (US)

(72) Inventors: Heejin Lee, Bedford, MA (US); Karen Daniel, Newton, MA (US); Matthew Sansone, Dracut, MA (US)

(73) Assignee: TARIS Biomedical LLC, Lexington, MA (US)

( * ) Notice: Subject to any disclaimer, the term of this patent is extended or adjusted under 35 U.S.C. 154(b) by 611 days.

(21) Appl. No.: 17/656,531

(22) Filed: Mar. 25, 2022

(65) Prior Publication Data

US 2022/0211987 A1    Jul. 7, 2022

Related U.S. Application Data

(60) Division of application No. 16/405,139, filed on May 7, 2019, now Pat. No. 11,285,304, which is a
(Continued)

(51) Int. Cl.
*A61M 31/00* (2006.01)
*A61K 9/00* (2006.01)
(Continued)

(52) U.S. Cl.
CPC ......... *A61M 31/002* (2013.01); *A61K 9/0024* (2013.01); *A61K 9/0034* (2013.01);
(Continued)

(58) Field of Classification Search
CPC .. A61M 31/002; A61M 31/007; A61M 31/00; A61M 2205/04; A61M 2210/1085;
(Continued)

(56) References Cited

U.S. PATENT DOCUMENTS

| | | |
|---|---|---|
| 2,118,631 A | 5/1938 | Wrappler |
| 3,279,996 A | 10/1966 | Long, Jr. et al. |

(Continued)

FOREIGN PATENT DOCUMENTS

| | | |
|---|---|---|
| DE | 3332156 | 3/1985 |
| EP | 3332156 | 3/1985 |

(Continued)

OTHER PUBLICATIONS

Park, Kinam, "A hydrophilic matrix approach for controlled vaginal drug delivery," Journal of Controlled Release, 224 (2016) p. 240.
(Continued)

*Primary Examiner* — Nilay J Shah
(74) *Attorney, Agent, or Firm* — Eversheds Sutherland (US) LLP

(57) ABSTRACT

Implantable drug delivery devices include a housing having a closed drug reservoir lumen bounded by a first wall structure and a hydrophilic second wall structure, and a drug contained in the drug reservoir lumen, wherein the first wall structure is impermeable to the drug and the second wall structure is permeable to the drug. Methods of providing controlled release of drug to a patient include deploying a drug delivery device in the patient releasing a drug from the drug reservoir lumen via diffusion through the second wall structure.

49 Claims, 26 Drawing Sheets

Related U.S. Application Data continuation of application No. 14/216,112, filed on Mar. 17, 2014, now Pat. No. 10,315,019.

(60) Provisional application No. 61/799,733, filed on Mar. 15, 2013.

(51) Int. Cl.

| | |
|---|---|
| *A61K 31/137* | (2006.01) |
| *A61K 31/167* | (2006.01) |
| *A61K 31/216* | (2006.01) |
| *A61K 31/337* | (2006.01) |
| *A61K 31/407* | (2006.01) |
| *A61K 31/438* | (2006.01) |
| *A61K 31/555* | (2006.01) |
| *A61K 31/7068* | (2006.01) |
| *A61K 33/243* | (2019.01) |
| *A61K 31/46* | (2006.01) |

(52) U.S. Cl.
CPC .......... *A61K 31/137* (2013.01); *A61K 31/167* (2013.01); *A61K 31/216* (2013.01); *A61K 31/337* (2013.01); *A61K 31/407* (2013.01); *A61K 31/438* (2013.01); *A61K 31/555* (2013.01); *A61K 31/7068* (2013.01); *A61K 33/243* (2019.01); *A61M 31/00* (2013.01); *A61M 31/007* (2013.01); *A61K 31/46* (2013.01); *A61M 2205/04* (2013.01); *A61M 2210/1085* (2013.01)

(58) Field of Classification Search
CPC ...... A61M 2210/1089; A61M 25/0041; A61M 27/008
See application file for complete search history.

(56) References Cited

U.S. PATENT DOCUMENTS

| | | |
|---|---|---|
| 3,786,813 A | 1/1974 | Michaels |
| 3,852,833 A | 12/1974 | Koneke et al. |
| 3,854,480 A | 12/1974 | Zaffaroni |
| 3,888,975 A | 6/1975 | Ramwell |
| 3,901,232 A | 8/1975 | Michaels et al. |
| 3,935,860 A | 2/1976 | Hoff |
| 4,014,335 A | 3/1977 | Arnold |
| 4,016,251 A | 4/1977 | Higuchi et al. |
| 4,210,670 A | 7/1980 | Cooke |
| 4,235,236 A | 11/1980 | Theeuwes |
| 4,392,848 A | 7/1983 | Lucas et al. |
| 4,449,980 A | 5/1984 | Millar et al. |
| 4,475,916 A | 10/1984 | Himmelstein |
| 4,605,412 A | 8/1986 | La Forest et al. |
| 4,629,449 A | 12/1986 | Wong |
| 4,655,219 A | 4/1987 | Petruzzi |
| 4,678,463 A | 7/1987 | Millar |
| 4,826,501 A | 5/1989 | Grundei |
| 4,871,542 A | 10/1989 | Vilhardt |
| 4,940,465 A | 7/1990 | Theeuwes et al. |
| 4,955,858 A | 9/1990 | Drews |
| 4,968,507 A | 11/1990 | Zenter et al. |
| 4,973,304 A | 11/1990 | Graham et al. |
| 5,005,591 A | 4/1991 | Austud |
| 5,062,829 A | 11/1991 | Pryor et al. |
| 5,066,290 A | 11/1991 | Measells et al. |
| 5,086,290 A | 2/1992 | Murray et al. |
| 5,146,933 A | 9/1992 | Boyd |
| 5,366,738 A | 11/1994 | Rork et al. |
| 5,441,550 A | 8/1995 | Hassenboehler, Jr. et al. |
| 5,499,997 A | 3/1996 | Sharpe et al. |
| 5,516,522 A | 5/1996 | Peyman et al. |
| 5,551,954 A | 9/1996 | Buscemi et al. |
| 5,629,008 A | 5/1997 | Lee et al. |
| 5,630,843 A | 5/1997 | Rosenberg |
| 5,697,974 A | 12/1997 | Wang |
| 5,700,288 A | 12/1997 | Eaton |
| 5,709,874 A | 1/1998 | Hanson et al. |
| 5,788,980 A | 8/1998 | Nabhi |
| 5,795,591 A | 8/1998 | Lee et al. |
| 5,797,898 A | 8/1998 | Santini, Jr. et al. |
| 5,830,230 A | 11/1998 | Breyman et al. |
| 5,851,217 A | 12/1998 | Wolff et al. |
| 5,855,906 A | 1/1999 | McClay |
| 5,869,081 A | 2/1999 | Jackanicz et al. |
| 5,972,372 A | 10/1999 | Saleh et al. |
| 5,989,581 A | 11/1999 | Groenwegen |
| 5,997,574 A | 12/1999 | Hayes et al. |
| 6,039,967 A | 3/2000 | Ottoboni et al. |
| 6,039,968 A | 3/2000 | Nabhi |
| 6,083,933 A | 7/2000 | Hahn |
| 6,086,909 A | 7/2000 | Harrison et al. |
| 6,139,535 A | 10/2000 | Greelis et al. |
| 6,171,298 B1 | 1/2001 | Matsuura et al. |
| 6,183,461 B1 | 2/2001 | Matsuura et al. |
| 6,207,180 B1 | 3/2001 | Ottoboni et al. |
| 6,283,998 B1 | 9/2001 | Eaton |
| 6,293,923 B1 | 9/2001 | Yachia et al. |
| 6,368,356 B1 | 4/2002 | Zhong et al. |
| 6,398,718 B1 | 6/2002 | Yachia et al. |
| 6,398,757 B1 | 6/2002 | Vareene et al. |
| 6,416,780 B1 | 7/2002 | Passmore et al. |
| 6,419,690 B1 | 7/2002 | Mikus et al. |
| 6,444,224 B1 | 9/2002 | Rathbone et al. |
| 6,458,069 B1 * | 10/2002 | Tam .................. A61K 51/1279 600/3 |
| 6,464,999 B1 | 10/2002 | Huo et al. |
| 6,482,837 B1 | 11/2002 | Wood |
| 6,491,666 B1 | 12/2002 | Santini, Jr. et al. |
| 6,524,608 B2 | 2/2003 | Ottoboni et al. |
| 6,537,193 B1 | 3/2003 | Lee et al. |
| 6,656,162 B2 | 12/2003 | Santini, Jr. et al. |
| 6,682,473 B1 | 1/2004 | Matsuura et al. |
| 6,695,830 B2 | 2/2004 | Vigil et al. |
| 6,712,784 B2 | 3/2004 | Huang |
| 6,730,072 B2 | 5/2004 | Shawgo et al. |
| 6,746,421 B2 | 6/2004 | Yachia et al. |
| 6,749,617 B1 | 6/2004 | Palasis et al. |
| 6,753,011 B2 | 6/2004 | Faour |
| 6,808,522 B2 | 10/2004 | Richards et al. |
| 6,875,208 B2 | 4/2005 | Santini, Jr. et al. |
| 6,899,890 B2 | 5/2005 | Kirschner et al. |
| 6,932,810 B2 | 8/2005 | Ryan |
| 6,949,125 B2 | 9/2005 | Robertson |
| 6,951,654 B2 | 10/2005 | Malcolm et al. |
| 6,973,718 B2 | 12/2005 | Sheppard, Jr. et al. |
| 6,976,950 B2 | 12/2005 | Connors et al. |
| 6,976,951 B2 | 12/2005 | Connors et al. |
| 6,988,983 B2 | 1/2006 | Connors et al. |
| 6,996,433 B2 | 2/2006 | Burbank et al. |
| 7,005,138 B2 | 2/2006 | Mahashabde et al. |
| 7,066,914 B2 | 6/2006 | Andersen |
| 7,074,178 B2 | 7/2006 | Connors et al. |
| 7,232,421 B1 | 6/2007 | Gambale et al. |
| 7,521,064 B2 | 4/2009 | Saxena et al. |
| 7,647,112 B2 | 1/2010 | Tracey et al. |
| 7,842,303 B2 | 11/2010 | Kuo et al. |
| 7,858,110 B2 | 12/2010 | Kuzma et al. |
| 7,862,552 B2 | 1/2011 | McIntyre et al. |
| 7,879,088 B2 | 2/2011 | Gao et al. |
| 8,167,836 B2 | 5/2012 | Lee et al. |
| 8,182,464 B2 | 5/2012 | Lee et al. |
| 8,303,977 B2 | 11/2012 | Kuzma et al. |
| 8,343,516 B2 | 1/2013 | Daniel et al. |
| 8,343,528 B2 | 1/2013 | Kuo et al. |
| 8,357,389 B2 | 1/2013 | Kuo et al. |
| 8,460,274 B2 | 6/2013 | Kuzma et al. |
| 8,529,936 B2 | 9/2013 | Kuo et al. |
| 8,658,195 B2 | 2/2014 | Kuo et al. |
| 8,690,840 B2 | 4/2014 | Lee et al. |
| 8,801,694 B2 | 8/2014 | Lee et al. |
| 9,061,125 B2 | 6/2015 | Watschke |
| 2001/0004709 A1 | 6/2001 | Dubrul |
| 2001/0041936 A1 | 11/2001 | Corbitt, Jr. et al. |

(56) References Cited

U.S. PATENT DOCUMENTS

| | | |
|---|---|---|
| 2002/0068897 A1 | 6/2002 | Jenkins et al. |
| 2002/0164734 A1 | 11/2002 | Jackson et al. |
| 2002/0183265 A1 | 12/2002 | Vogt et al. |
| 2003/0015203 A1 | 1/2003 | Makower et al. |
| 2003/0059456 A1 | 3/2003 | Malcolm et al. |
| 2003/0064095 A1 | 4/2003 | Martin et al. |
| 2003/0077310 A1 | 4/2003 | Pathak et al. |
| 2003/0118649 A1 | 6/2003 | Gao et al. |
| 2003/0118692 A1 | 6/2003 | Wang et al. |
| 2003/0139800 A1 | 7/2003 | Campbell |
| 2003/0144734 A1 | 7/2003 | Dreschnack et al. |
| 2003/0147936 A1 | 8/2003 | Sahadevan |
| 2003/0229263 A1 | 12/2003 | Connors et al. |
| 2004/0013702 A1 | 1/2004 | Glover |
| 2004/0022824 A1 | 2/2004 | Li et al. |
| 2004/0034332 A1 | 2/2004 | Uhland |
| 2004/0037318 A1 | 2/2004 | Salin et al. |
| 2004/0149294 A1 | 8/2004 | Gianchandani et al. |
| 2004/0220552 A1 | 11/2004 | Heruth et al. |
| 2004/0260272 A1 | 12/2004 | Friedman et al. |
| 2005/0228482 A1 | 10/2005 | Herzog et al. |
| 2005/0234013 A1 | 10/2005 | Parsons |
| 2005/0234431 A1 | 10/2005 | Williams et al. |
| 2005/0238733 A1 | 10/2005 | Henry |
| 2005/0251108 A1 | 11/2005 | Frassica |
| 2005/0273164 A1 | 12/2005 | Bowman et al. |
| 2006/0105010 A1 | 5/2006 | Rahe et al. |
| 2006/0122689 A1 | 6/2006 | Kocur et al. |
| 2006/0217656 A1 | 9/2006 | Freyman et al. |
| 2006/0234978 A1 | 10/2006 | Marcum |
| 2006/0259118 A1 | 11/2006 | Pal et al. |
| 2006/0264897 A1 | 11/2006 | Lob et al. |
| 2006/0264912 A1 | 11/2006 | McIntyre et al. |
| 2007/0172507 A1 | 7/2007 | Zupkas et al. |
| 2007/0172508 A1 | 7/2007 | Zupkas et al. |
| 2007/0196423 A1 | 8/2007 | Ruane |
| 2007/0202151 A1 | 8/2007 | Lee |
| 2007/0254014 A1 | 11/2007 | Ahmed et al. |
| 2007/0255222 A1 | 11/2007 | Li et al. |
| 2007/0275035 A1 | 11/2007 | Herman et al. |
| 2008/0004578 A1 | 1/2008 | Hixon et al. |
| 2008/0051740 A1 | 2/2008 | Sokal et al. |
| 2008/0091176 A1 | 4/2008 | Alessi et al. |
| 2008/0119729 A1 | 5/2008 | Copa et al. |
| 2008/0233167 A1 | 9/2008 | Li et al. |
| 2008/0234659 A1 | 9/2008 | Cheng et al. |
| 2008/0312636 A1 | 12/2008 | Miller et al. |
| 2009/0004246 A1 | 1/2009 | Woolfson et al. |
| 2009/0149833 A1* | 6/2009 | Cima ............... A61K 31/167 604/93.01 |
| 2009/0171465 A1 | 7/2009 | Bucay-Couto et al. |
| 2009/0187254 A1 | 7/2009 | Deal et al. |
| 2009/0208540 A1* | 8/2009 | Kuzma ............. A61K 9/0024 514/282 |
| 2009/0247992 A1 | 10/2009 | Shalon et al. |
| 2009/0292237 A1 | 11/2009 | Overstreet et al. |
| 2010/0003297 A1 | 1/2010 | Tobias et al. |
| 2010/0010627 A1 | 1/2010 | Matheny |
| 2010/0060309 A1 | 3/2010 | Lewis |
| 2010/0076261 A1 | 3/2010 | Neeman et al. |
| 2010/0080835 A1 | 4/2010 | Kuzma |
| 2010/0119694 A1 | 5/2010 | Guo et al. |
| 2010/0145467 A1 | 6/2010 | Davoudi et al. |
| 2010/0152704 A1 | 6/2010 | Lee et al. |
| 2010/0330149 A1 | 12/2010 | Daniel et al. |
| 2010/0331770 A1* | 12/2010 | Lee .................. A61K 9/0034 221/199 |
| 2011/0060309 A1* | 3/2011 | Lee .................. A61K 9/0092 514/626 |
| 2011/0106248 A1 | 5/2011 | Kokott et al. |
| 2011/0112475 A1 | 5/2011 | Benson |
| 2011/0137244 A1 | 6/2011 | Lee et al. |
| 2011/0152839 A1 | 6/2011 | Cima et al. |
| 2011/0171272 A1 | 7/2011 | Li et al. |
| 2011/0202036 A1 | 8/2011 | Boyko et al. |
| 2011/0218488 A1 | 9/2011 | Boyoko et al. |
| 2011/0236456 A1 | 9/2011 | Kuzma |
| 2011/0244015 A1 | 10/2011 | Kuzma et al. |
| 2012/0089121 A1 | 4/2012 | Lee et al. |
| 2012/0089122 A1 | 4/2012 | Lee et al. |
| 2012/0191068 A1 | 7/2012 | Himes et al. |
| 2012/0203203 A1 | 8/2012 | Lee et al. |
| 2013/0131637 A1 | 5/2013 | DiCesare |
| 2013/0158675 A1 | 6/2013 | Hutchins, III et al. |
| 2013/0302397 A1 | 11/2013 | Kuzma |
| 2014/0012222 A1 | 1/2014 | Kuzma |
| 2014/0209100 A1 | 7/2014 | Kiser et al. |
| 2015/0080847 A1 | 3/2015 | Cima et al. |

FOREIGN PATENT DOCUMENTS

| | | |
|---|---|---|
| EP | 0572932 | 9/2000 |
| WO | 95/33511 | 12/1995 |
| WO | 97/44021 A1 | 11/1997 |
| WO | 98/31415 | 7/1998 |
| WO | 99/18884 | 4/1999 |
| WO | 00/40234 | 7/2000 |
| WO | 01/67991 | 9/2001 |
| WO | 02/05800 | 6/2002 |
| WO | 02/085428 | 10/2002 |
| WO | 03/009882 | 2/2003 |
| WO | 03/024357 | 3/2003 |
| WO | 02/00203 | 10/2003 |
| WO | 2004037318 | 7/2004 |
| WO | 2005032524 | 4/2005 |
| WO | 2005115245 | 12/2005 |
| WO | 2006/121969 | 11/2006 |
| WO | 2007115259 | 10/2007 |
| WO | 2008051889 | 5/2008 |
| WO | 2008115536 | 2/2009 |
| WO | 2008/038281 | 5/2009 |
| WO | 2009/076547 A1 | 6/2009 |
| WO | 2009/076547 A2 | 6/2009 |
| WO | 2009029958 | 6/2009 |
| WO | 2010/105093 | 9/2010 |
| WO | 2011/031855 A2 | 3/2011 |
| WO | 2012/019155 A1 | 2/2012 |
| WO | 2016/028774 A1 | 2/2016 |

OTHER PUBLICATIONS

Teller, Ryan S., et al., "Controlling the hydration rate of hydrophilic matrix in the core of an intravaginal ring determines antiretroviral release," Journal of Controlled Release, 224 (2016), pp. 176-183.
Appell, Rodeney A. et al., "339—A Novel Intravesical Device for Optimal Drug Delivery," The Journal of Urology, vol. 163, No. 4, Supplement, Sunday, Apr. 30, 2000, pp. 77.
Berman, et al., "Lidocaine Permeability in Silicone Tissue Expanders: An in Vitro Analysis," Plastic and Reconstructive Surgery; 84(4) (Oct. 1989), pp. 621-623.
Grayson, et al., "Molecular release from a polymeric microreservoir device: Influence of chemistry, polymer swelling, and loading on device performance," J. Biomed Mat Res, vol. 69A, No. 3, pp. 502-512, Jun. 2004.
McGuire, et al., "In Vivo Diffusion of Lidocaine Through Tissue Expanders," Plastic and Reconstructive Surgery, 89(4):675-678, Apr. 1992.
Sconzo, et al. "In Vitro Diffusion of Lidocaine across Endotracheal Tube Cuffs," Regional Anesthesia, (Jan.-Feb. 1990), pp. 37-40.
Woolfson, et al., "Design of a Silicone Reservoir Intravaginal Ring for the Delivery of Oxybutynin," Journal of Controlled Release, pp. 465-476, vol. 61, Elsevier Science B.V, Sep. 2003.
Park, Kinam, "A hydrophilic matrix approach for controlled vaginal drug delivery," Journal of Controlled Release, 224 (Feb. 2016) p. 240.
Search Report of Singapore Patent Application No. 11201507294W dated Jul. 29, 2016.
Written Opinion of Singapore Patent Application No. 11201507294W dated Aug. 18, 2016.

(56) References Cited

OTHER PUBLICATIONS

PCT International Search Report and Written Opinion for PCT Application No. PCT/US2014/030437 mailed Sep. 1, 2014 (12 pages).

\* cited by examiner

DRUG DELIVERY DEVICES WITH DRUG-PERMEABLE COMPONENT AND METHODS

CROSS-REFERENCE TO RELATED APPLICATIONS

This application is a divisional of U.S. patent application Ser. No. 16/405,139, filed May 7, 2019, issued as U.S. Pat. No. 11,285,304 on Mar. 29, 2022, which is a continuation of U.S. patent application Ser. No. 14/216,112, filed Mar. 17, 2014, issued as U.S. Pat. No. 10,315,019 on Jun. 11, 2019, which claims the benefit of U.S. Provisional Patent Application No. 61/799,733, filed Mar. 15, 2013, each of which is incorporated herein by reference.

BACKGROUND

The present disclosure is generally in the field of implantable medical devices, and more particularly relates to drug-delivery devices with a drug-permeable component.

Implantable medical devices and methods are known for targeted, e.g., local or regional, drug delivery in order to avoid the problems associated with systemic drug delivery. Local delivery of drug to some tissue sites, however, has room for improvement, particularly with respect to extended drug delivery with minimally invasive devices and methods with minimum patient discomfort from the presence of the device itself. The problem is particularly acute for certain drugs, e.g., those having relatively low water solubility, and/or for certain therapies in which the drug needs to be controllably released at therapeutic levels over an extended periods of several days or weeks, while keeping the devices sufficiently small to avoid unnecessary discomfort and pain during and following deployment of the device into patient.

U.S. Patent Application Publications No. 2012/0203203 (TB 121), No. 2012/0089122 (TB 117), No. 2011/0060309 (TB 108), No. 2011/0152839 (TB 112), and No. 2010/0331770 (TB 101) by TARIS Biomedical Inc. describe various drug delivery devices that provide controlled release of drug from a housing. The device may be free floating in a patient's bladder, yet tolerably and wholly retained in the patient's bladder while locally releasing the drug over an extended period. It would be desirable, however, to provide new designs of intravesical drug delivery devices, and other implantable devices capable of delivering drugs at effective release rates for a range of different drugs.

SUMMARY

In one aspect, implantable drug delivery devices are provided, including a housing having a closed drug reservoir lumen bounded by a first wall structure and a hydrophilic second wall structure, and a drug contained in the drug reservoir lumen, wherein the first wall structure is impermeable to the drug, and the second wall structure is permeable to the drug. In one embodiment, the first wall structure is a cylindrical tube and the second wall structure is an end wall disposed at at least one end of the cylindrical tube. In another embodiment, the first wall structure and the second wall structure are adjacent one another and together form a cylindrical tube.

In another aspect, methods of providing controlled release of drug to a patient are provided, including (i) deploying a drug delivery device in the patient, the device comprising a closed drug reservoir lumen bounded by a first wall structure and a hydrophilic second wall structure, and (ii) releasing a drug from the drug reservoir lumen via diffusion through the second wall structure, wherein the first wall structure is impermeable to the drug, and the second wall structure is permeable to the drug. In one embodiment, the first wall structure is a cylindrical tube and the second wall structure is an end wall disposed at at least one end of the cylindrical tube. In another embodiment, the first wall structure and the second wall structure are adjacent one another and together form a cylindrical tube.

DETAILED DESCRIPTION

Figure 1:
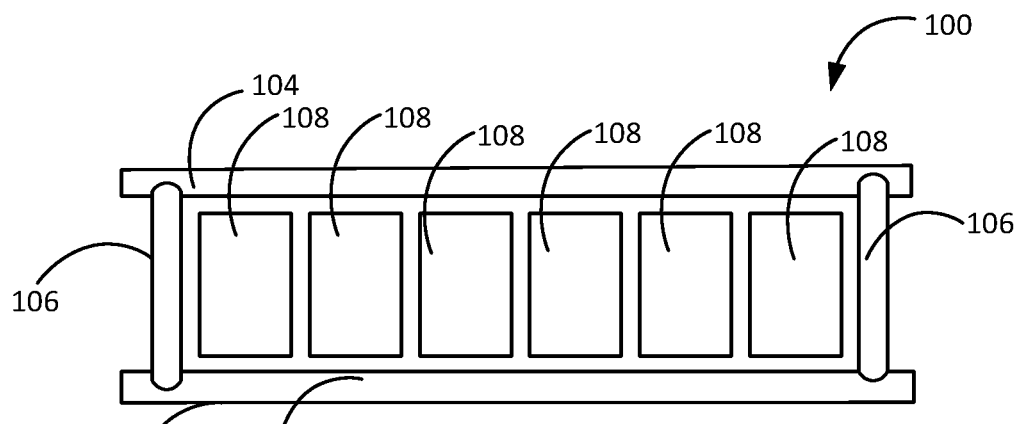
FIG. 1 is a cross-sectional plan view of one embodiment of an implantable drug delivery device wherein the second wall structure is an end wall.

Improved implantable drug delivery devices are provided. In a particular embodiment, the devices are configured for intravesical insertion and sustained drug delivery, preferably providing a zero order release rate of therapeutically effective amounts of the drug.

It was discovered that it may be difficult to achieve a zero order release rate beyond three to four days with osmotic pressure delivery mechanisms for certain drugs. In experiments, after three to four days, the drug release rate quickly decreased, which can cause the drug urine concentration in the bladder to fall below a minimum effective concentration before the end of treatment period. It is not always feasible to extend the period of zero order release simply by providing more, or more densely packed, osmotic agent with the drugs, for example due to overall implant system size limitations. It is also not always feasible to instead provide overall first order drug release during an entire treatment period, because it may not be safe to have the initial peak drug release rate high enough that even with the decay of the drug release rate toward the end of the treatment period, the release rate is still above minimum effective concentration of the drug.

Accordingly, the particular devices described herein have been developed, wherein instead of an osmotic drug release mechanism, drug release is controlled by drug diffusion through a drug-permeable polymer or matrix component defining part of the device housing. In one embodiment, the device includes a drug-permeable polymer component.

In one aspect, an implantable drug delivery device is provided that includes a housing having a closed drug reservoir lumen bounded by a first wall structure and a hydrophilic second wall structure; and a drug contained in the drug reservoir lumen, wherein the first wall structure is permeable or impermeable to water and impermeable to the drug, and the second wall structure is permeable to the drug. The walls bounding and defining the drug reservoir of the device are made of a first material that serves as the first wall structure and a second material that serves as the second wall structure, such that drug release occurs essentially only through the second material. In one embodiment, the device does not include an aperture; drug release is only by diffusion through the second wall structure. As used herein, the terms "impermeable to the drug" and "impermeable to water" refer to the wall structure being substantially impermeable to the drug or to water, such that essentially no drug or water is released via the wall structure over the therapeutic release period.

For use in the bladder, it is important that the device be compliant (i.e., easily flexed, soft feeling) during detrusor muscle contraction in order to avoid or mitigate discomfort and irritation to the patient. Thus, it is noted the durometer of the first and second materials of construction are important, and the proportion of a high durometer material may be limited in constructing a device housing of a given size while keeping it suitably compliant in the bladder. For example, Tecophilic™ thermoplastic polyurethane (Lubrizol Corp.) may have a Shore hardness greater than 70 A, such as from 80 A to 65D, while silicone tubing which may have a Shore hardness of from 50 A to 70 A. Accordingly, it can be advantageous to utilize the combination of these two different polymeric materials, rather than making the device entirely of the water-swelling hydrophilic, drug-permeable second material.

In a preferred embodiment, the device is elastically deformable between a relatively straightened shape suited for insertion through the urethra of a patient and into the patient's bladder and a retention shape suited to retain the device within the bladder. In one embodiment, the device further includes retention frame lumen and a retention frame positioned in the retention frame lumen. In embodiments, a retention frame may include two or more housing units.

The first wall structure may be formed of a silicone. For example, the housing may include a silicone tube, the wall of the silicone tube serving as the first wall structure. In other embodiments, the first wall structure may be formed of other water permeable materials. In a preferred embodiment, the drug is in a solid form (e.g., a tablet or plurality of tablets) and the first wall structure is water permeable to permit in vivo solubilization of the drug while in the drug reservoir lumen. For example, the first wall structure may be formed of silicone having a Shore durometer value from about 50 A to about 70 A.

The second wall structure is a hydrophilic polymer, which is designed to absorb water. For example, the second wall structure may be a hydrophilic elastomeric material, which is at least partially made of hydrophilic polyurethane, hydrophilic polyesters, or hydrophilic polyamides. In a preferred embodiment, the second wall structure includes a thermoplastic polyurethane, such as Tecophilic™ thermoplastic polyurethane, HydroThane™ thermoplastic polyurethane (AdvanSource Biomaterials Corp.), Quadraphilic™ thermoplastic polyurethane (Biomerics, LLC) (ALC grades are aliphatic polycarbonate-based and ALE grades are aliphatic polyether-based hydrophilic polyurethanes), HydroMed™ (AdvanSource Biomaterials Corp.), or Dryflex® (HEXPOL TPE). Another hydrophilic polymer is polyether block amide Pebax® MV 1074 SA 01 MED (Arkema), which is a thermoplastic elastomer made of flexible and hydrophilic polyether and rigid polyamide. For example, the hydrophilic material of the second wall structure may have a Shore durometer value from about 70 A to about 65D. The particular material and its thickness and wall area can be selected to achieve a particular drug release profile, i.e., water and drug permeation rates.

The arrangement of the first and second wall structures can take a variety of forms. Non-limiting examples are shown in FIGS. 1-12C. In certain embodiments, the first wall structure is a cylindrical tube and the second wall structure is an end wall disposed at least one end of the cylindrical tube, or the first wall structure and the second wall structure are adjacent one another and together form a cylindrical tube. That is, drug release is controlled by drug diffusion through a drug-permeable component defining a portion of the closed device housing. The drug-permeable wall structure may be located, dimensioned, and have material properties to provide the desired rate of controlled drug diffusion from the device.

In one embodiment, as shown in FIGS. 1-8B, the first wall structure is a cylindrical tube and the second wall structure is an end wall disposed at least one end of the cylindrical tube. In certain embodiments, the first wall structure is a cylindrical tube and the second wall structure is an end wall disposed at least one end of the cylindrical tube and the second wall structure is in the form of a disk stabilized in a lumen of the cylindrical tube. As shown, the first wall structure may be in the form of a cylindrical tube and the second wall structure may be in the form of a disk at one or both ends. The disk may be stabilized in the lumen of the cylindrical tube using a variety of mechanical or adhesive means. For example, the disk may be stabilized in the lumen of the cylindrical tube via frictional engagement between the disk and the tube, notches in the interior wall of the tube, a suitable adhesive, or one or more washers or other structural stabilizing members. In certain embodiments, the first wall structure, the one or more washers or stabilizing members, and/or the adhesive are made of silicone.

Figure 2:
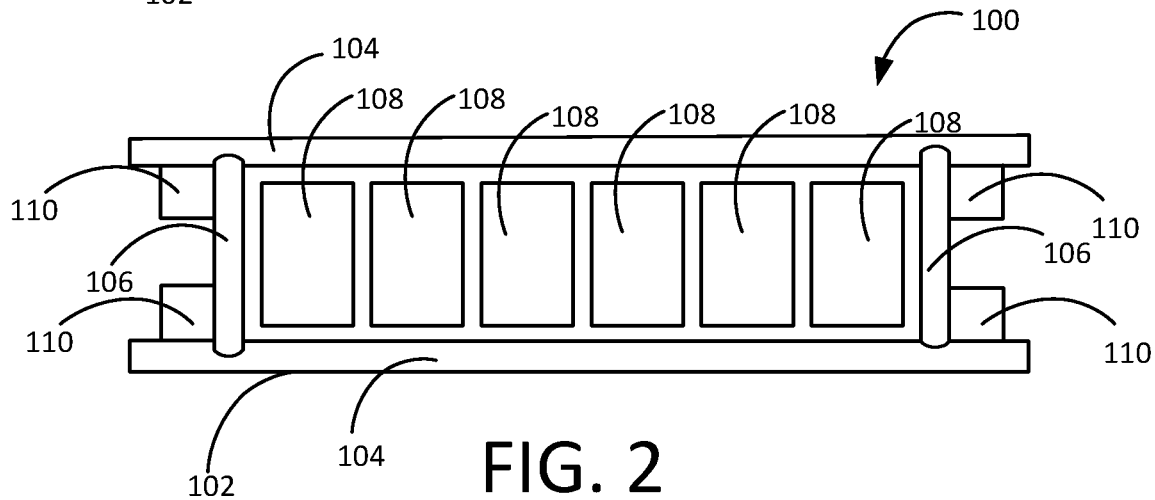
FIG. 2 is a cross-sectional plan view of one embodiment of an implantable drug delivery device wherein the second wall structure is an end wall.
Figure 3:
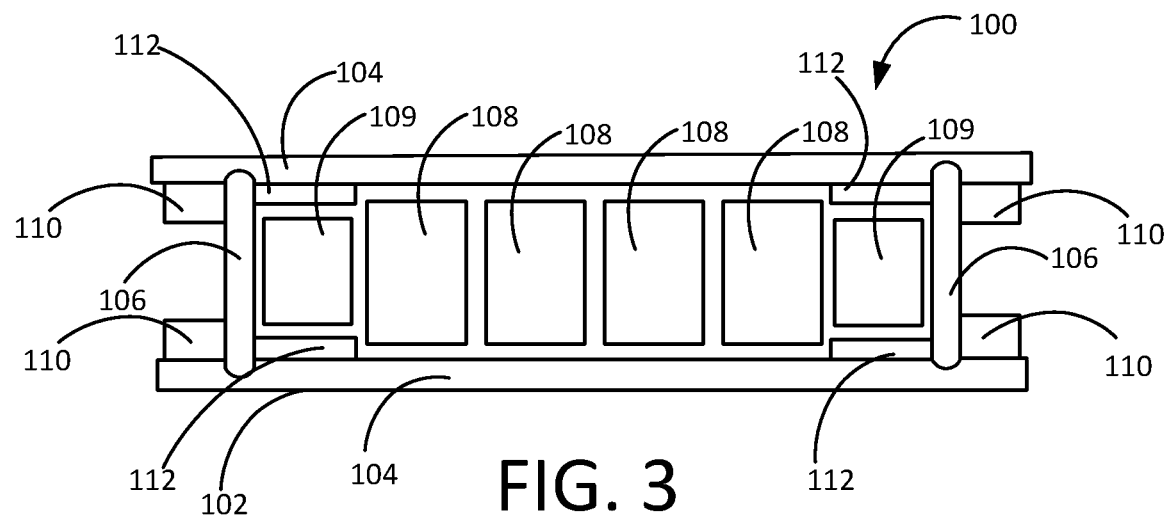
FIG. 3 is a cross-sectional plan view of one embodiment of an implantable drug delivery device wherein the second wall structure is an end wall.

FIGS. 1-3 show an implantable drug delivery device 100 including a housing 102 having a closed drug reservoir lumen bounded by a first wall structure 104 and a hydrophilic second wall structure 106, and a drug 108, in the form of a plurality of drug tablets, contained in the drug reservoir lumen, wherein the first wall structure 104 is impermeable to the drug, and the second wall structure 106 is permeable to the drug. The second wall structure 106 is an end wall disposed at at least one end of the first wall structure 104, which is a cylindrical tube. The second wall structure 106 is in the form of a disk that is stabilized in a lumen of the cylindrical tube 104. As shown in FIG. 1, the disk 106 may be friction fit or adhered to the lumen of the cylindrical tube 104. As shown in FIG. 2, outer washer 110 is adjacent to disk 106 and stabilizes it within the lumen of the cylindrical tube 104. As shown in FIG. 3, outer washer 110 and inner washer 112 may sandwich disk 106 and stabilize it within the lumen of the cylindrical tube 104. As shown in FIG. 3, the drug tablets 109 adjacent the inner washer 112 may have a decreased tablet diameter relative to the other drug tablets 108, so as to fit within the inner diameter of the inner washer 112. The drug tablets 109 may be skipped and in such case, there will be a void space in the inner washer 112, which may create induction or lag time before drug release starts. Depending on the void space in the inner washer 112, the lag time can be varied or controlled.

Figure 4A:
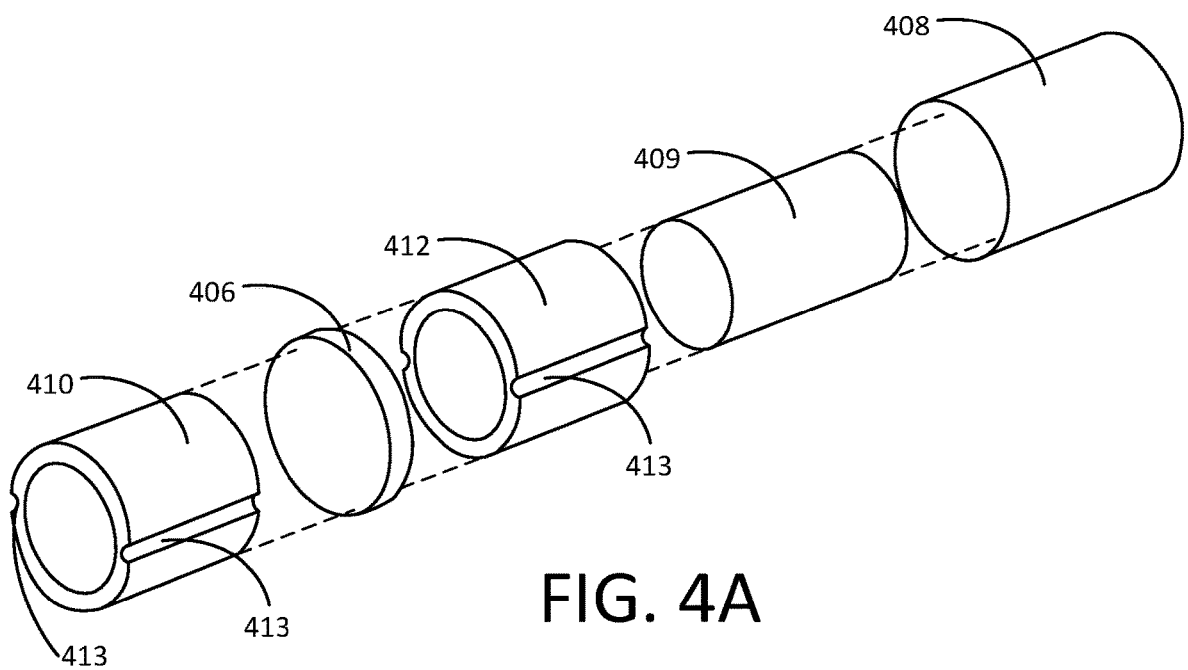
FIG. 4A is an exploded perspective view of a portion of one embodiment of an implantable drug delivery device wherein the second wall structure is an end wall.
Figure 4B:
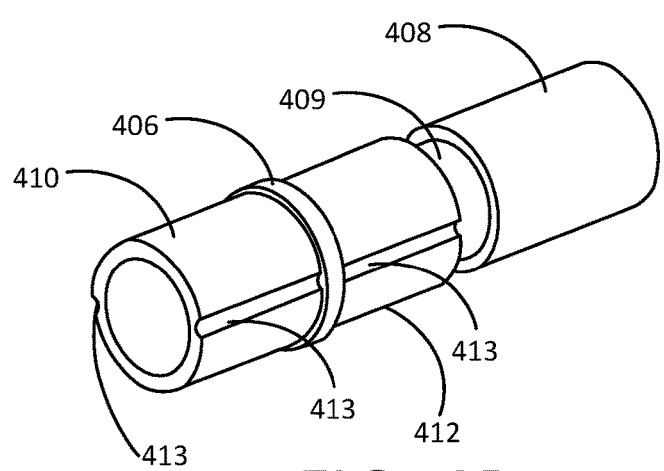
FIG. 4B is a perspective view of the portion of the device of FIG. 4A.
Figure 4C:
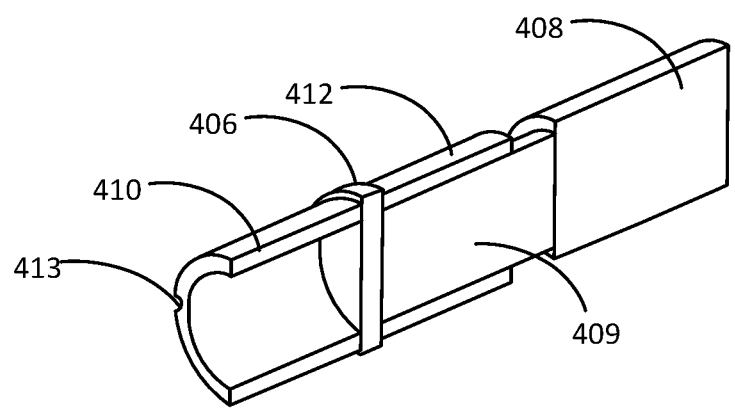
FIG. 4C is a cross-sectional perspective view of the portion of the device of FIG. 4B.
Figure 4D:
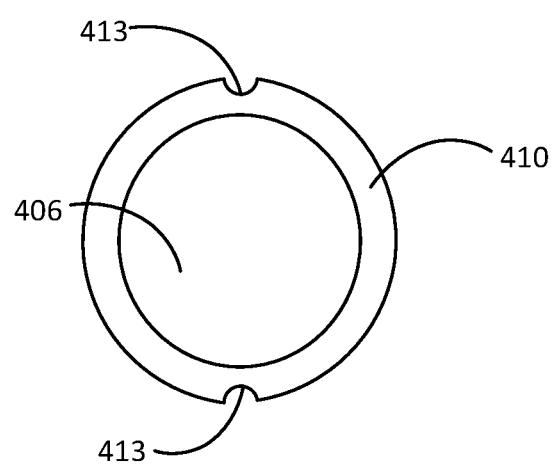
FIG. 4D is a cross-sectional view of the portion of the device of FIG. 4B.

The disk-stabilizing washer component can take a variety of forms. Non-limiting examples are shown in FIGS. 4A-7. As shown in FIGS. 4A-4D, inner and outer washers 412, 410 may sandwich disk 406. The drug tablet 409 adjacent the inner washer 412 may have a decreased tablet diameter relative to the other drug tablets 408, so as to fit within the inner diameter of the inner washer 412. The washers 410, 412, the disk 406, and the drug tablets 408, 409 may then be disposed within a cylindrical tube (i.e., the first wall structure). For example, the inner and outer washers may be made of silicone, and the hydrophilic disk may be Tecophilic™. In one embodiment, the washers have an inner diameter of 2.16 mm and an outer diameter of 2.77 mm, and the drug tablets have diameters of 2.16 mm and 2.64 mm. In certain embodiments, as shown in FIGS. 4A-4C, the washers 410, 412 include one or more grooves 413 to receive an adhesive (e.g., room temperature vulcanizing (RTV) silicone). In one embodiment, the grooves have a diameter of 0.3 mm. For example, the adhesive may be applied at one or both of the inner and outer washers. The inner surface of outer washer 410 may be covered with hydrophilic material to aid the initial wetting of such surface once in contact with water or bodily fluid. For example, the inner surface of the outer washer may be covered with water soluble excipients, such as sodium chloride, urea, polyvinylpyrrolidone (PVP), or polyethylene glycol (PEG), either in a powder form or a tablet form, which may fit the void space in the outer washer. In addition, the inner surface of the outer washer can be coated with hydrophilic polymers used to construct the second wall structure. Appropriate hydrophilic coating method varies depending on the substrate condition of the inner surface of the outer washer.

Figure 5:
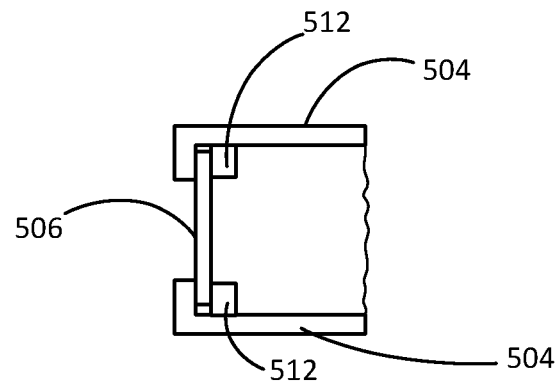
FIG. 5 is a partial cross-sectional plan view of one embodiment of an implantable drug delivery device wherein the second wall structure is an end wall.

As shown in FIG. 5, in one embodiment, the first wall structure 504 is a cylindrical tube having an inner diameter at the end of the tube that is smaller than the inner diameter of the remainder of the tube. As shown in FIG. 5, the inner diameter of the end of the cylindrical tube 504 may be smaller than the diameter of the disk 506, such that the end of the cylindrical tube 504 stabilizes the disk 506 on one side. Inner washer 512 may be used to stabilize the disk 506 on the other side.

Figure 6:
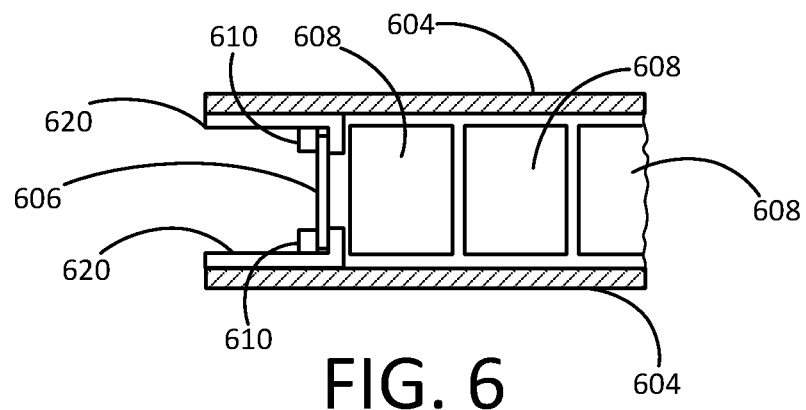
FIG. 6 is a partial cross-sectional plan view of one embodiment of an implantable drug delivery device wherein the second wall structure is an end wall.

As shown in FIG. 6, in one embodiment, the first wall structure is a cylindrical tube 604 having a housing insert 620. The housing insert 620 is fixed in the cylindrical tube 604 to stabilize the disk 606 from one side. As shown in FIG. 6, the housing insert 620 may be cylindrical in shape and have an outer diameter such that the insert 620 may be secured within the cylindrical tube 604. The inner diameter of an end of the cylindrical housing insert 620 may be smaller than the diameter of the disk 606, such that the end of the insert 620 stabilizes the disk 606 on one side. Outer washer 610 may be disposed within the housing insert 620 to stabilize the disk 606 on the other side. Drug tablets 608 may be provided in the lumen of the cylindrical tube 604.

Figure 7:
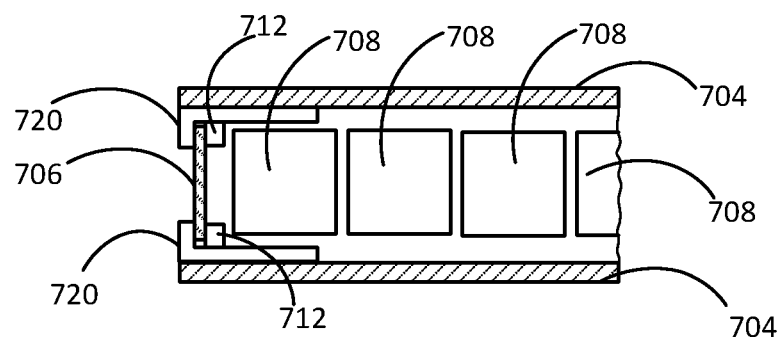
FIG. 7 is a partial cross-sectional plan view of one embodiment of an implantable drug delivery device wherein the second wall structure is an end wall.

FIG. 7 illustrates another embodiment of a device having a housing insert 720. Housing insert 720 is fixed in cylindrical tube 704 to stabilize the disk 706 from one side. Inner washer 712 stabilizes the disk 706 from the other side. Drug tablets 708 are provide in the lumen of the cylindrical tube 704 and insert 720.

FIG. 8 illustrates one embodiment of a drug delivery device 800 having a washer-stabilized disk 806 at each end of the device. The disks 806 are stabilized between inner washers 812 and outer washers 810. Drug tablets are provided within the lumen of cylindrical tube 804, with the drug tablets 809 adjacent to the disks 806 having a smaller diameter than tablets 808.

Thus, the assembly of a device in which a closed housing is formed by a cylindrical tube first wall structure and an end wall second wall structure, may take many forms. Given a specific drug formulation, the following parameters may be tailored to affect the release profile of the drug: disk material, thickness, and diameter; inner washer inner diameter, outer diameter, and length; outer washer inner diameter, outer diameter, and length; initial void space in the inner washer (e.g., a larger void may result in a longer release lag time). For example, the inner washer and the outer washer may be fixed in a silicone tube so that the disk is stabilized in both longitudinal directions. In one embodiment, the washers are made of a high durometer silicone (e.g., MED-4780 by Nusil Technology LLC) and a silicone adhesive (e.g., MED3-4213 by Nusil Technology LLC) is applied at the interface between the washer and tube.

The hydrophilic polymer wall structure tends to absorb water and swell, and the degree of swelling depends on water absorption behavior of the polymer. Therefore, disk wall thickness can be selected based on the type of hydrophilic polymer used and its degree of water absorption, to achieve a desired drug release rate. Initial void space in the inner washer can also be used to program a lag time in the drug release profile. Overall, to decrease the release rate of a drug through a disk, the disk diameter, inner washer inner diameter, and outer washer inner diameter may be decreased, and the length(s) of the outer and/or inner washers, and the disk thickness may be increased.

In other embodiments, as shown in FIGS. 9-12C, the first wall structure and the second wall structure are adjacent one another and together form a cylindrical tube. For example, such devices may be formed in a coextrusion process. In one embodiment, the coextruded first and second wall structures are thermoplastic polymers possessing the desired properties.

Figure 9:
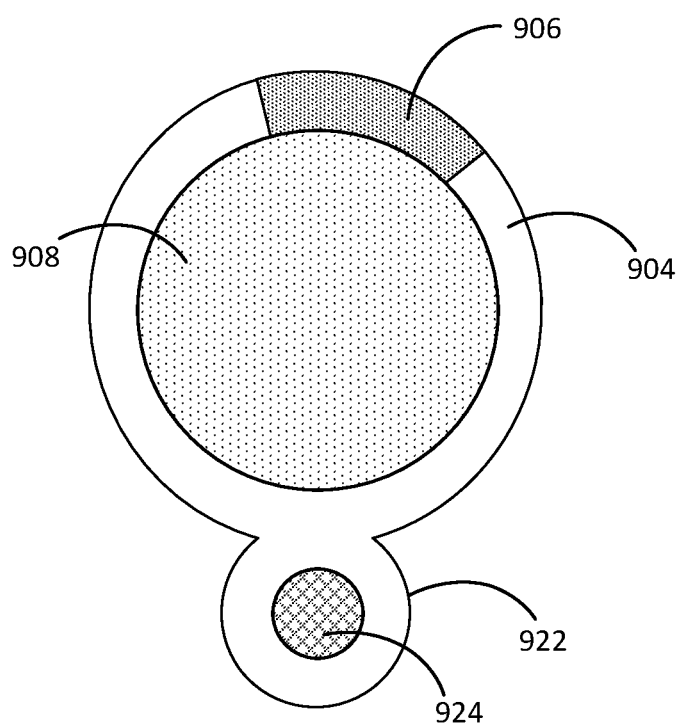
FIG. 9 is a cross-sectional view of one embodiment of an implantable drug delivery device wherein the first and second wall structures together form a cylindrical tube.

As shown in FIG. 9, the first wall structure 904 and second wall structure 906 together form a cylindrical tube having a lumen in which drug formulation 908 is contained. The second wall structure 906 is in the form of a strip extending along at least a portion of the length of the first wall structure 904 and is permeable to the drug, while the first wall structure 904 is not permeable to the drug. In certain embodiments, multiple hydrophilic strips or regions may be used in a single device.

Figure 10A:
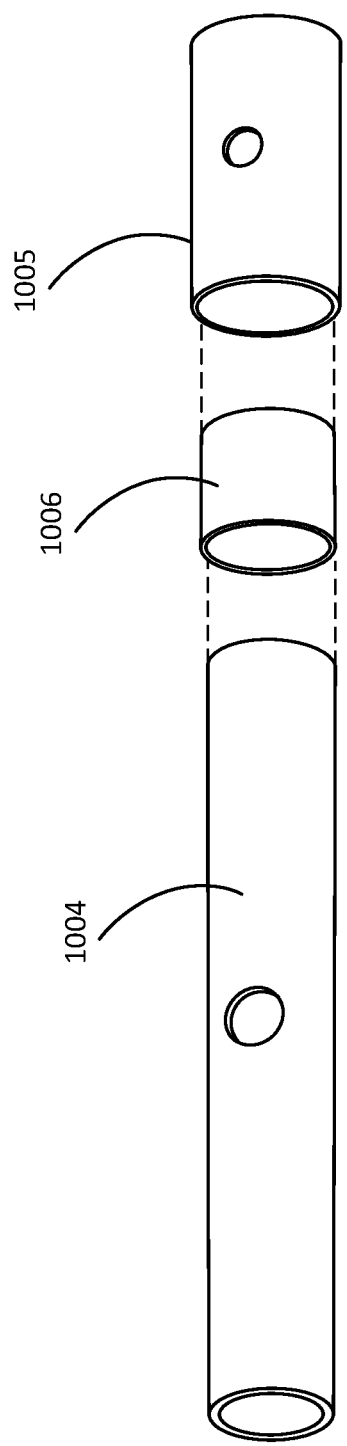
FIG. 10A is an exploded perspective view of one embodiment of an implantable drug delivery device wherein the first and second wall structures together form a cylindrical tube.
Figure 10B:
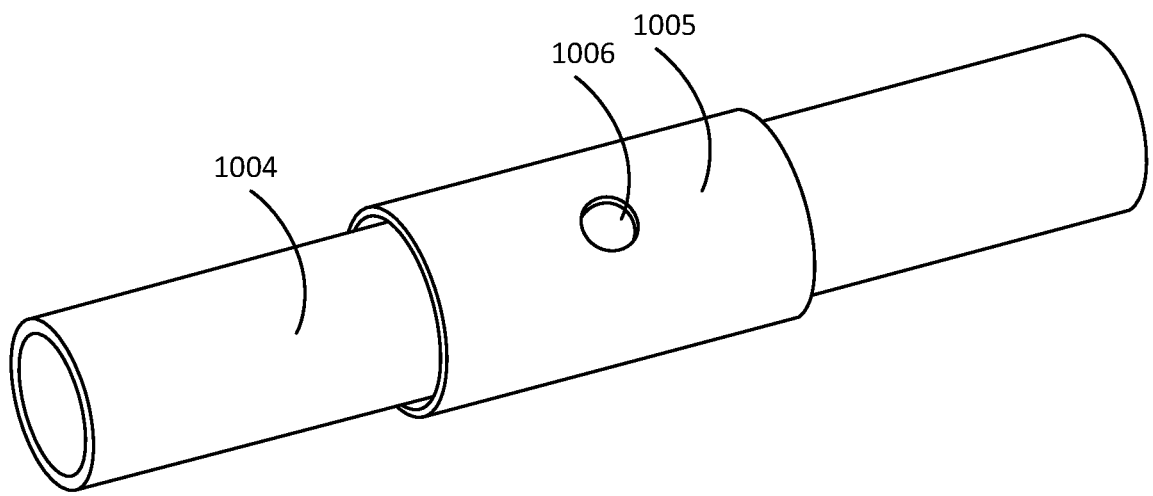
FIG. 10B is a perspective view of the device of FIG. 10A.
Figure 10C:
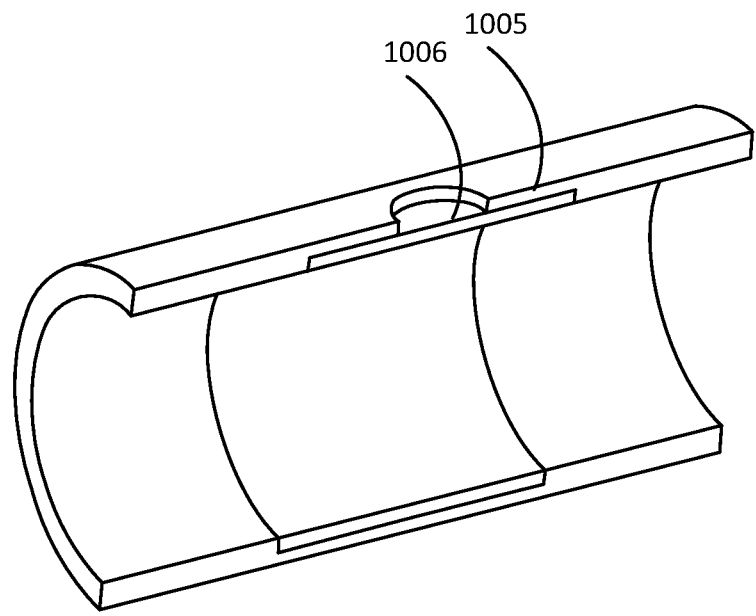
FIG. 10C is a partial cross-sectional perspective view of the device of FIG. 10B.

FIGS. 10A-10C illustrate another embodiment of a device in which the first wall structure 1004 forms a closed cylindrical tube with second wall structure 1006. In FIGS. 10A-10C, first wall structure 1004 is in the form of a tube having an aperture in a sidewall thereof. Hydrophilic band 1006 is sized and shaped to fit within sleeve 1005, which has an aperture similarly sized to that of the first wall structure 1004. Hydrophilic band 1006 is disposed around tube 1004 such that the hydrophilic material covers the aperture in the tube 1004, thereby forming a closed cylindrical tube therewith. Sleeve 1005 may be disposed over the band 1006 to stabilize the band 1006, while exposing the band 1006 by aligning the aperture of the sleeve 1005 with the aperture of the first wall structure 1004 to allow release of the drug. For example, an adhesive may be applied to the lumen of the sleeve to adhere the sleeve and band assembly to the first wall structure. As shown in FIG. 10C, the inner diameter of the hydrophilic second wall band 1006 may be flush with the inner diameter of the sleeve 1005, which has a notch therein to accommodate the band 1006. In certain embodiments, the first wall structure tube, the sleeve, and/or the adhesive are made of silicone, while the hydrophilic band is made of a thermoplastic polyurethane, such as Tecophilic™.

Figure 11A:
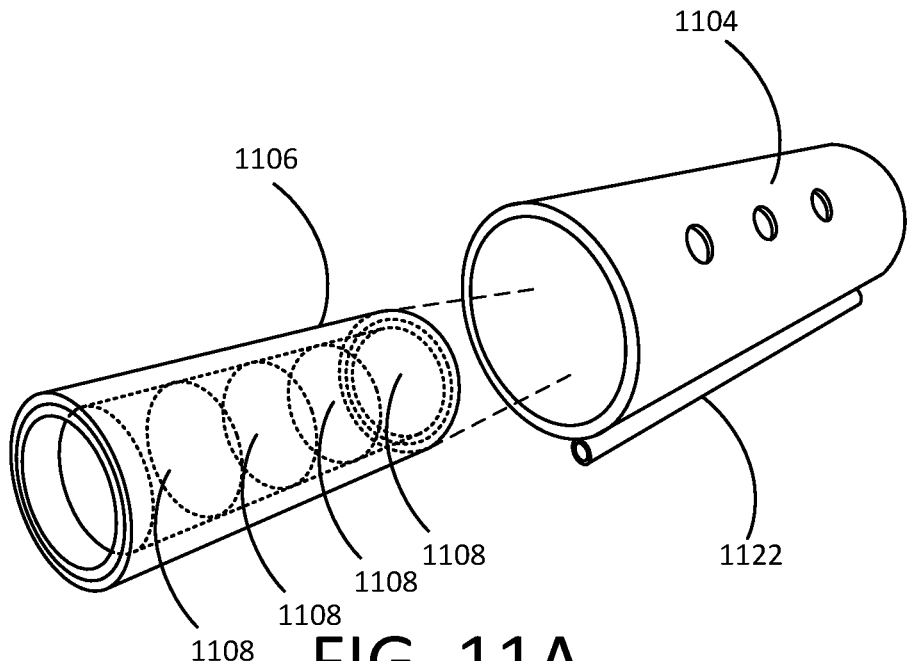
FIG. 11A is an exploded perspective view of one embodiment of an implantable drug delivery device wherein the first and second wall structures together form a cylindrical tube.
Figure 11B:
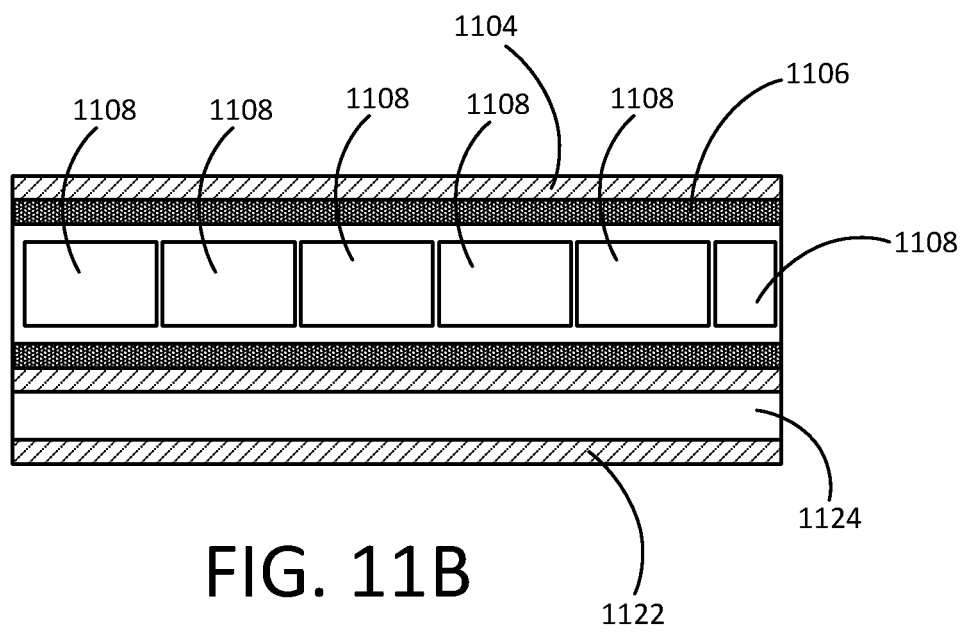
FIG. 11B is a cross-sectional plan view of the device of FIG. 11A.

FIGS. 11A-11B illustrate another embodiment of a device in which the first wall structure 1104 forms a closed cylindrical tube with second wall structure 1106. First wall structure 1104 is in the form of a tube having three apertures in a sidewall thereof. Hydrophilic second wall structure 1106 is in the form of a tube containing drug tablets 1108. Hydrophilic tube 1106 is sized and shaped to fit within the first wall structure tube 1104, such that the hydrophilic material of the tube 1106 is disposed at each of the apertures of the first wall structure 1104, thereby forming a closed cylindrical tube therewith. For example, the first wall structure tube may have one or more apertures therein. In certain embodiments, the first wall structure has one, two, three, or more apertures therein.

Figure 12A:
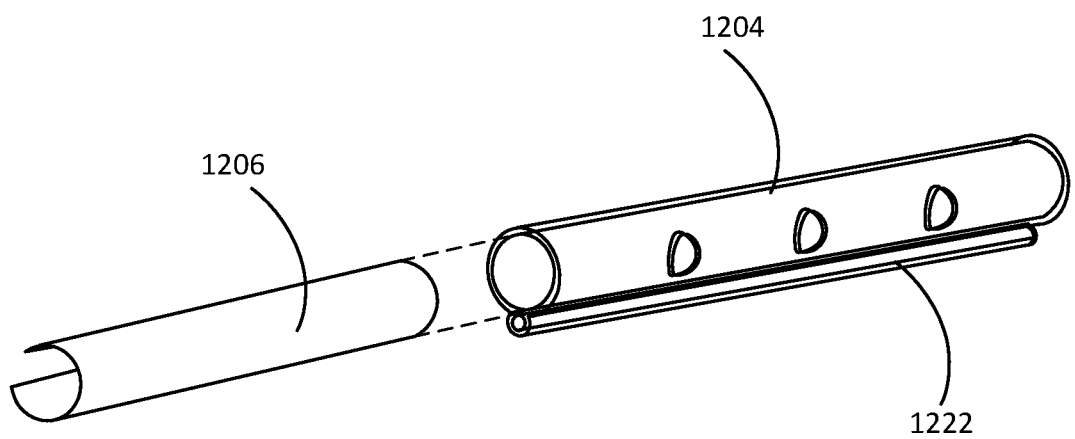
FIG. 12A is an exploded perspective view of one embodiment of an implantable drug delivery device wherein the first and second wall structures together form a cylindrical tube.
Figure 12B:
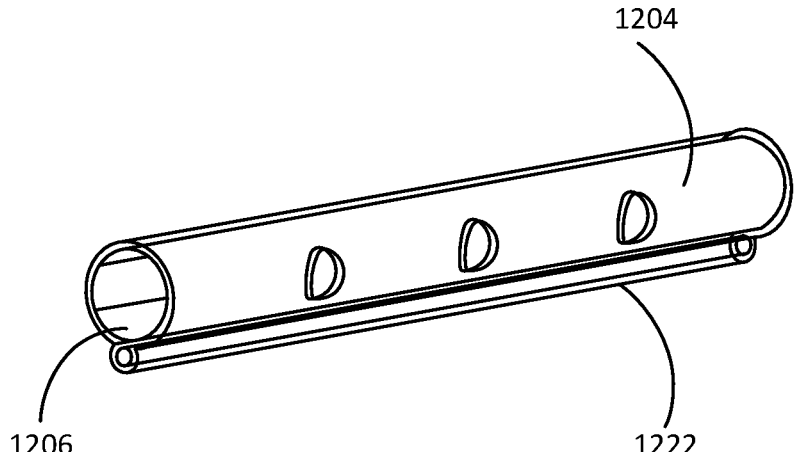
FIG. 12B is a perspective view of the device of FIG. 12A.
Figure 12C:
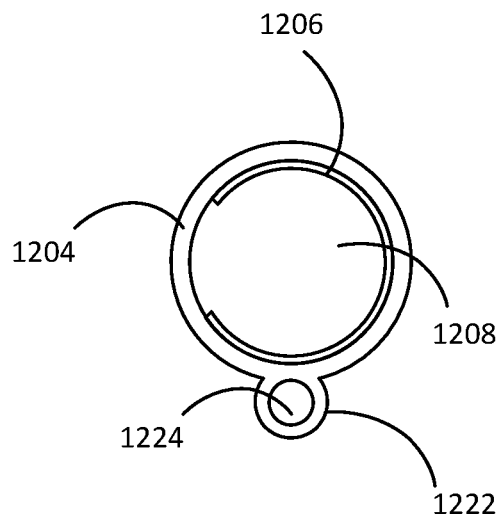
FIG. 12C is a cross-sectional view of the device of FIG. 12B.
Figure 13:
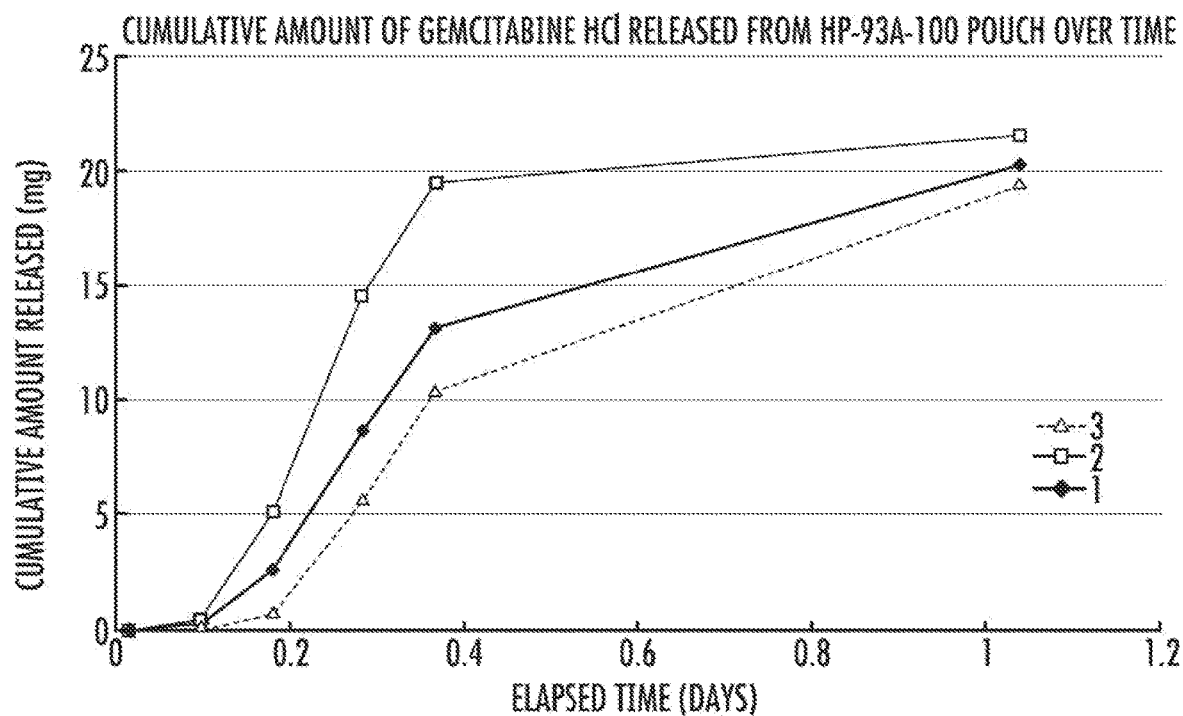
FIG. 13 is a graph showing the cumulative amount of gemcitabine HCl released from a HP-93A-100 pouch over time.
Figure 14:
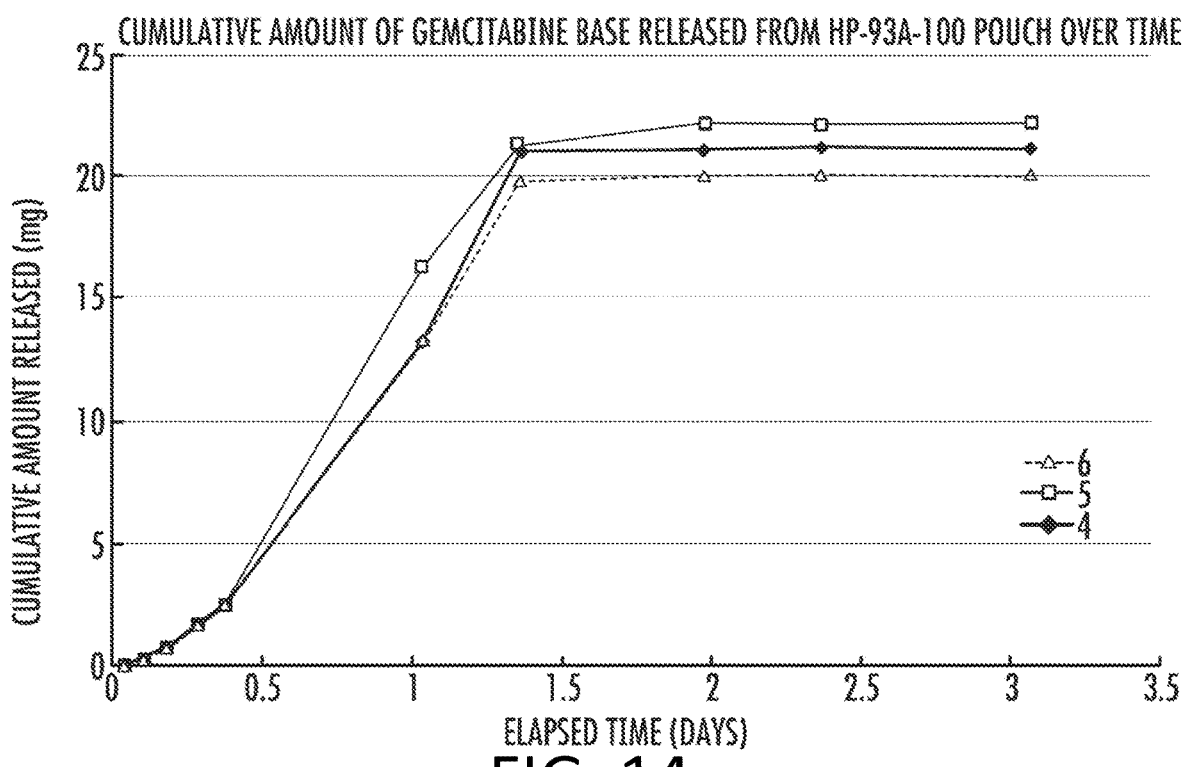
FIG. 14 is a graph showing the cumulative amount of gemcitabine base released from a HP-93A-100 pouch over time.
Figure 15:
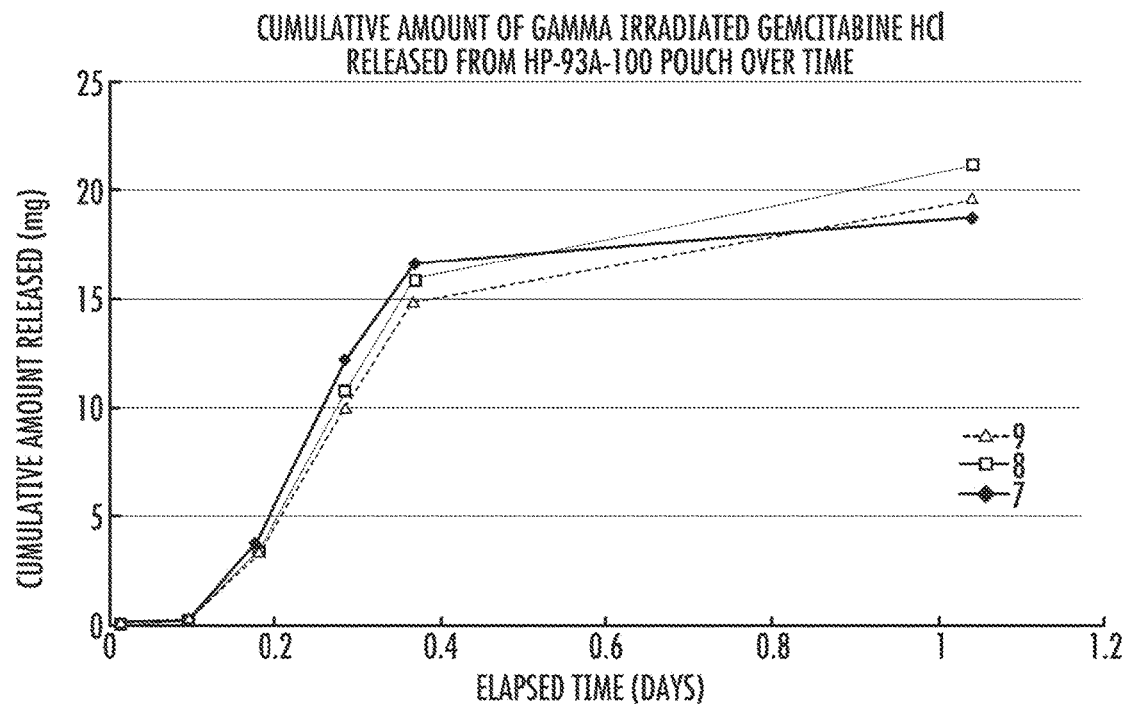
FIG. 15 is a graph showing the cumulative amount of gamma irradiated gemcitabine HCl released from a HP-93A-100 pouch over time.
Figure 16:
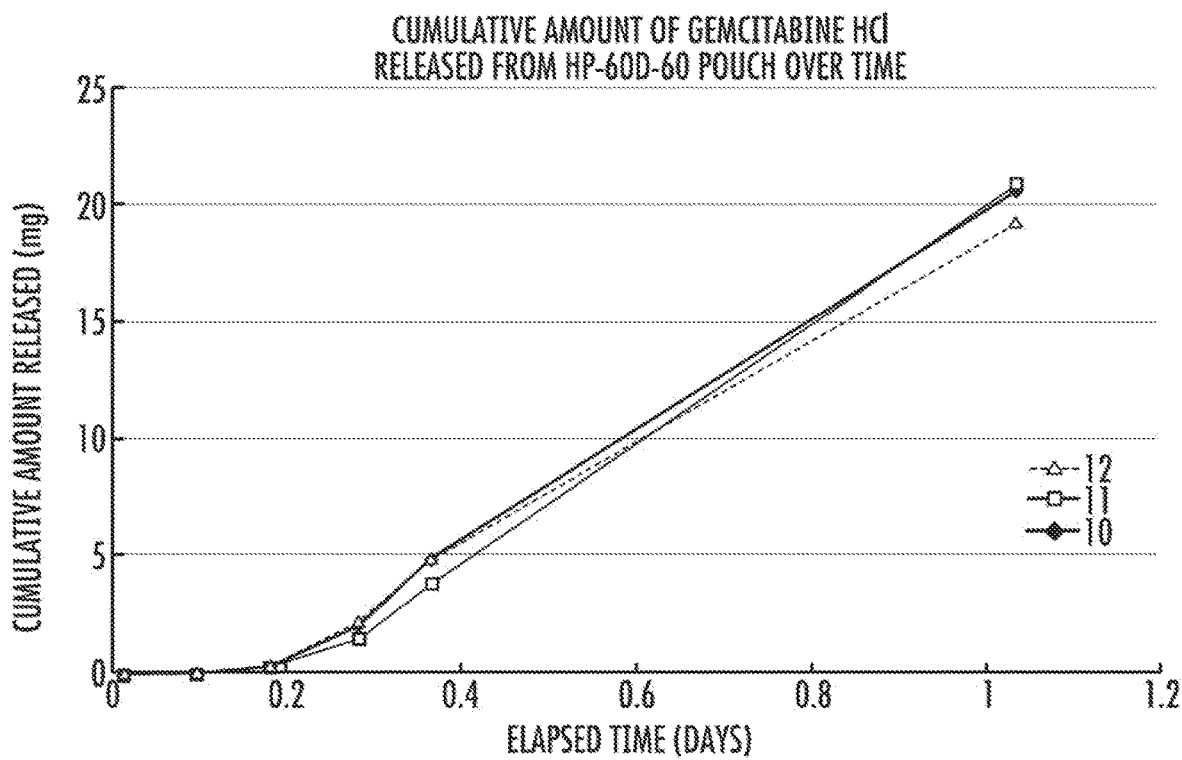
FIG. 16 is a graph showing the cumulative amount of gemcitabine HCl released from a HP-60D-60 pouch over time.
Figure 17:
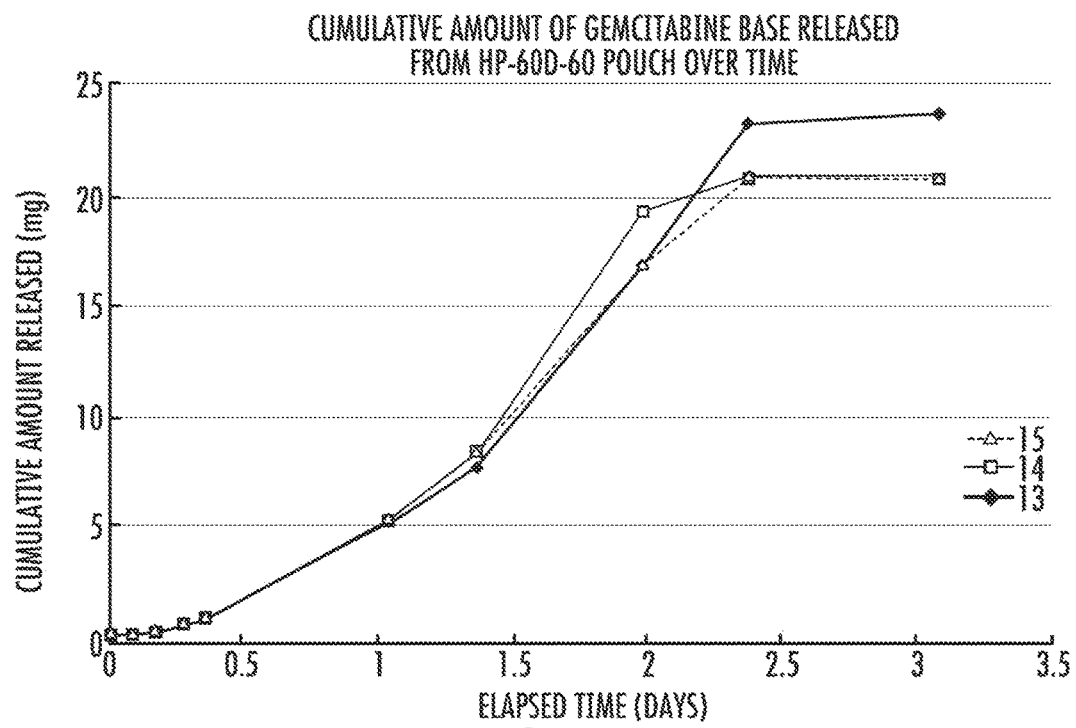
FIG. 17 is a graph showing the cumulative amount of gemcitabine base released from a HP-60D-60 pouch over time.
Figure 18:
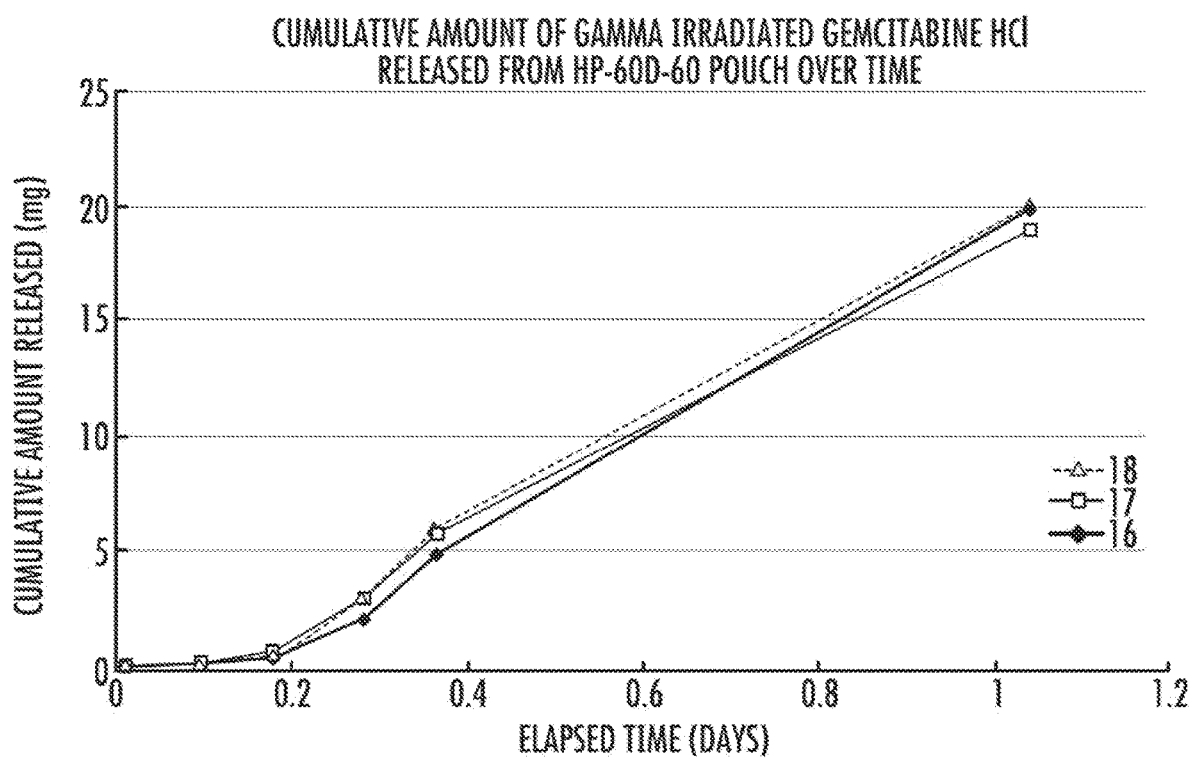
FIG. 18 is a graph showing the cumulative amount of gamma irradiated gemcitabine HCl released from a HP-60D-60 pouch over time.
Figure 19:
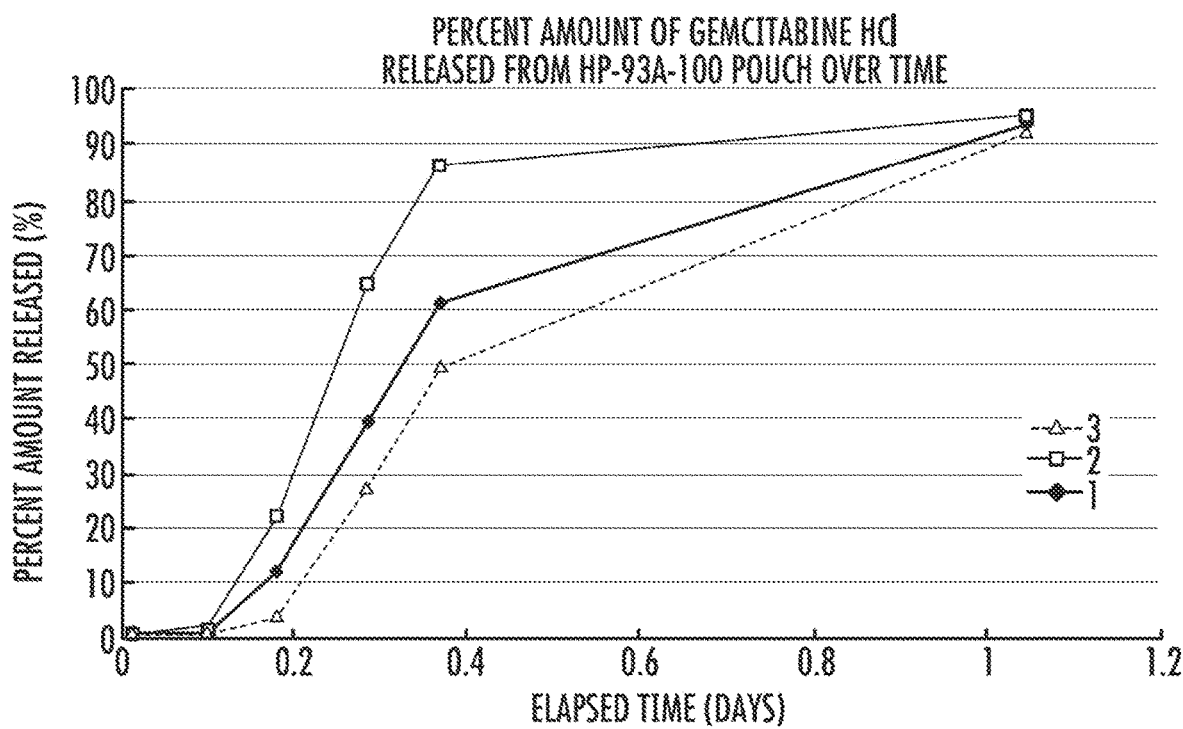
FIG. 19 is a graph showing the percent amount of gemcitabine HCl released from a HP-93A-100 pouch over time.
Figure 20:
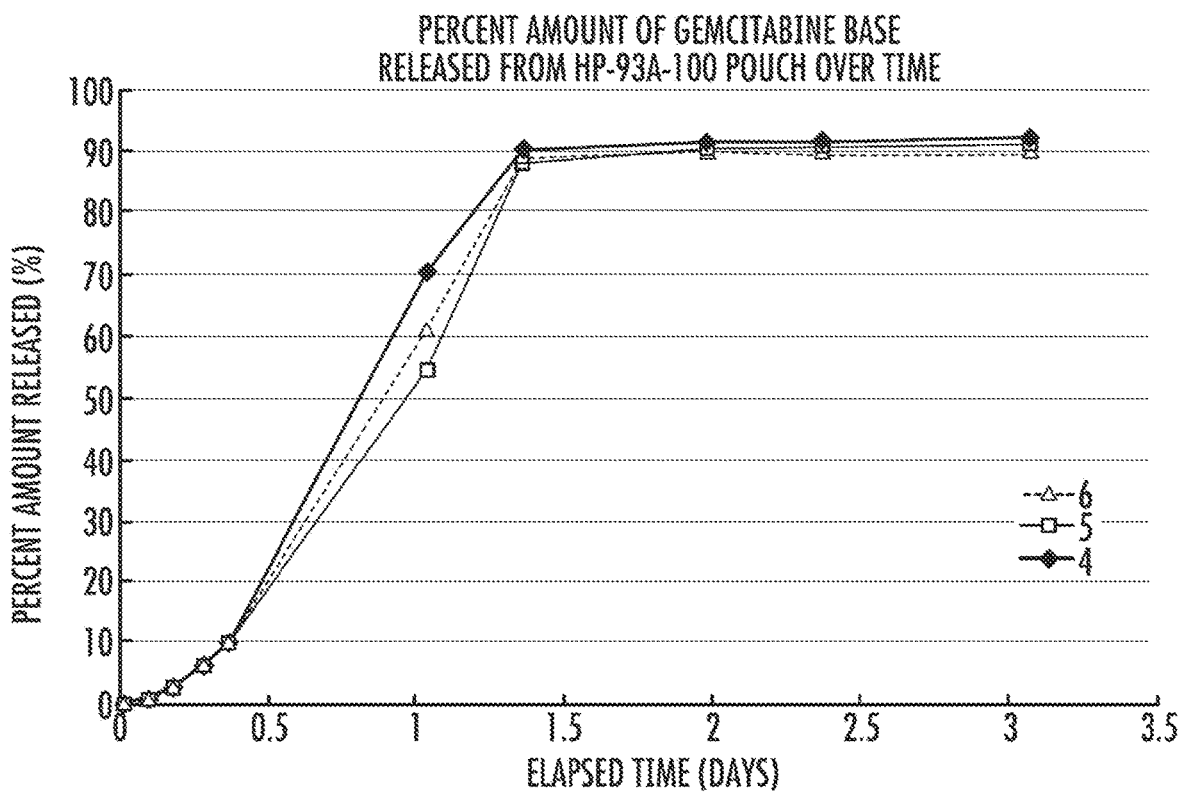
FIG. 20 is a graph showing the percent amount of gemcitabine base released from a HP-93A-100 pouch over time.
Figure 21:
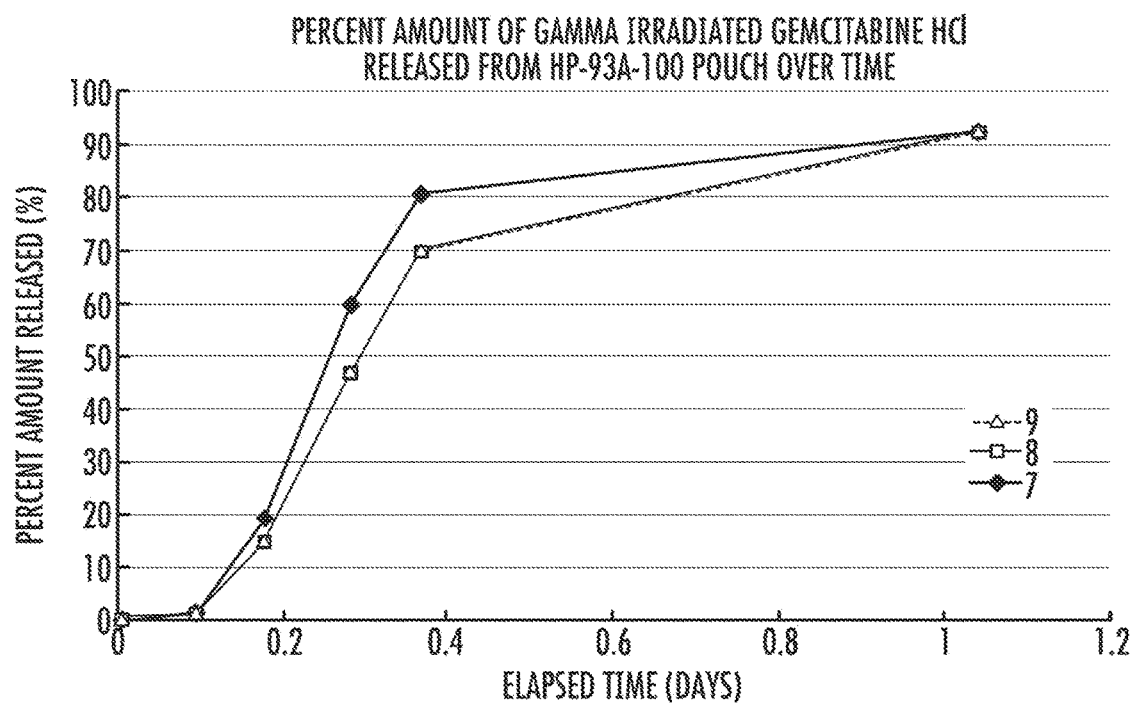
FIG. 21 is a graph showing the percent amount of gamma irradiated gemcitabine HCl released from a HP-93A-100 pouch over time.
Figure 22:
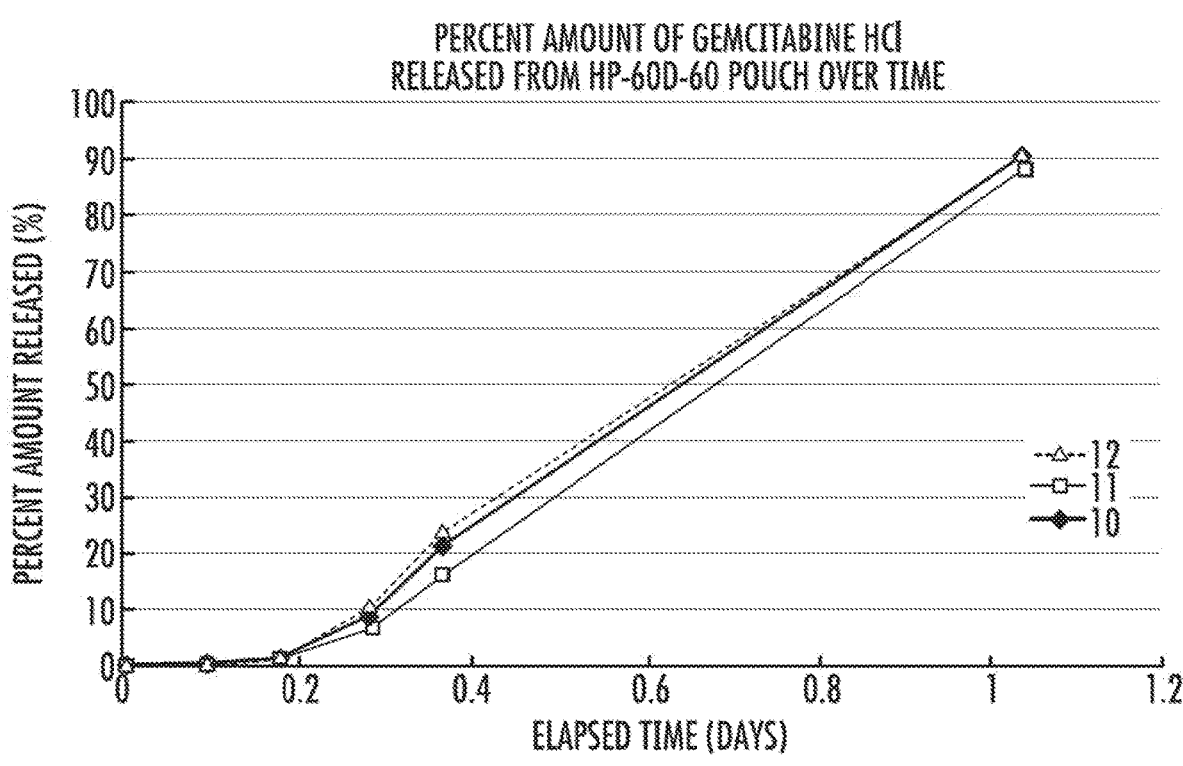
FIG. 22 is a graph showing the percent amount of gemcitabine HCl released from a HP-60D-60 pouch over time.
Figure 23:
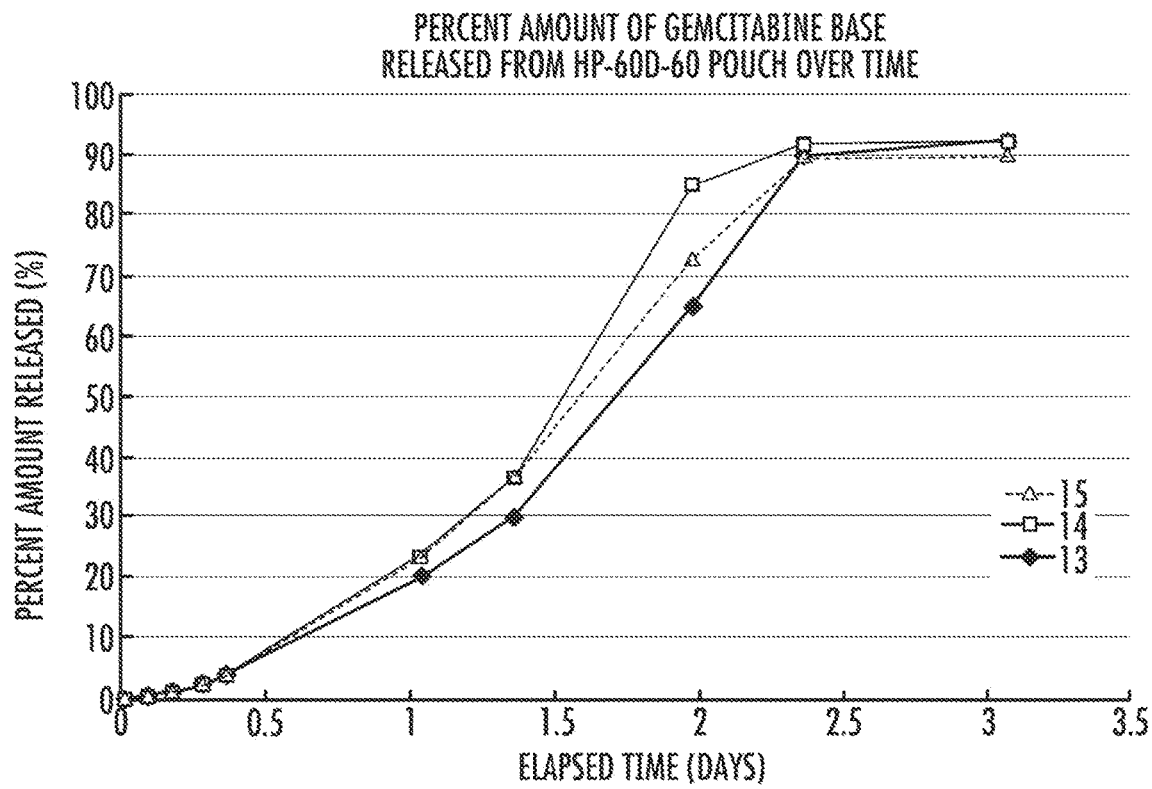
FIG. 23 is a graph showing the percent amount of gemcitabine base released from a HP-60D-60 pouch over time.
Figure 24:
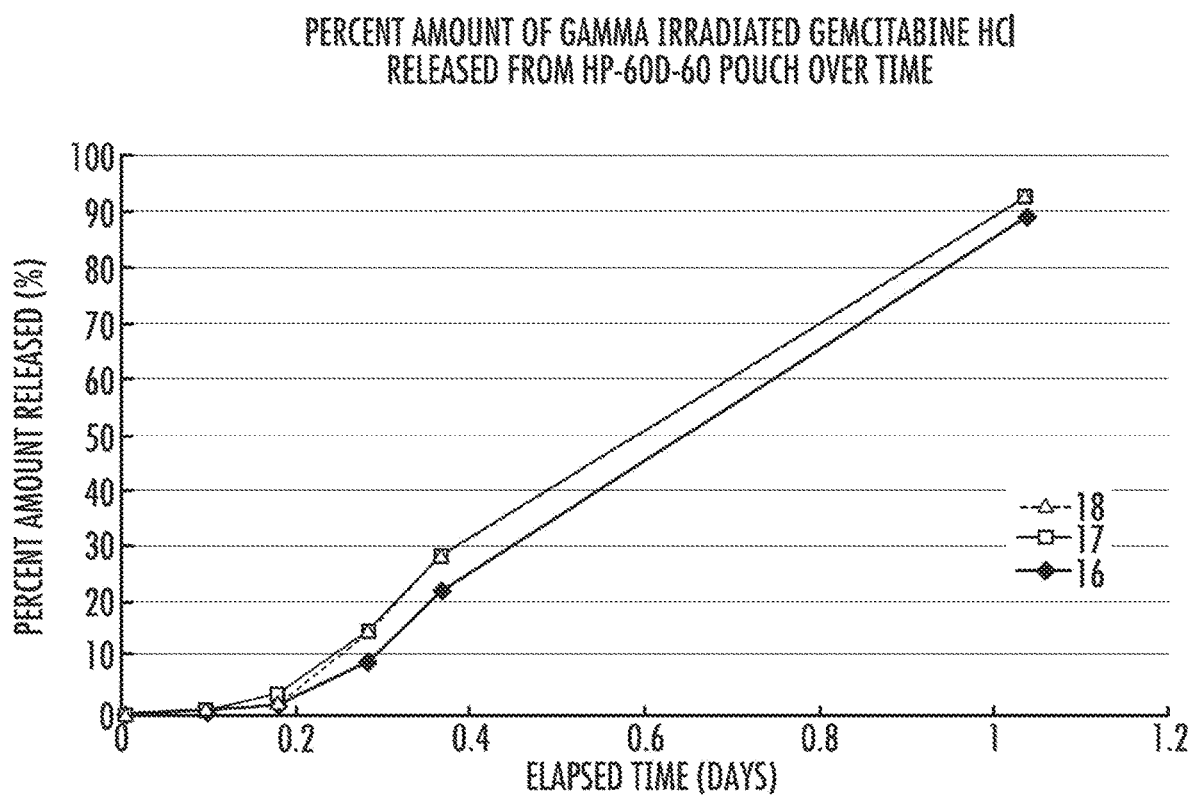
FIG. 24 is a graph showing the percent amount of gamma irradiated gemcitabine HCl released from a HP-60D-60 pouch over time.

FIGS. 12A-12C illustrate another embodiment of a device in which the first wall structure 1204 forms a closed cylindrical tube with hydrophilic second wall structure 1206. First wall structure 1204 is in the form of a tube having three apertures in a sidewall thereof. Hydrophilic second wall structure 1206 is a semi-cylindrical insert that is sized and shaped to fit within the tube 1204, such that hydrophilic second wall 1206 is disposed at each of the apertures of the tube 1204, thereby forming a closed cylindrical tube therewith. The hydrophilic second wall structure may take the form of a thin strip that is sized to extend along only the circumference of the tube containing the apertures. Alternatively, the hydrophilic second wall structure may extend from about 50 percent to about 100 percent of the circumference of the tube containing the apertures. In certain embodiments, the tube is silicone while the hydrophilic insert structure is a thermoplastic polyurethane, such as Tecophilic™.

Thus, the size, shape, thickness, and material properties of the second wall structure may be selected to achieve a desired drug release rate. Moreover, in the embodiments utilizing an aperture-exposed second wall structure, the size and number of the aperture(s) may also be selected to achieve a desired drug release rate.

In embodiments in which the first and second wall structures together form a cylindrical tube, any suitable end plugs or closures may be used to seal the ends of the tube after the drug is loaded. These end plugs/closures ensure that the hydrophilic polymer portions exposed at the external surface of the tube (e.g., by forming a portion of the external tube or by being exposed via apertures in the external tube) are the only path for drug release. In embodiments in which the second wall structure forms an end wall of the tube, no end plug or closure is present at the end(s) which include the second wall structure(s). That is, in embodiments in which the second wall structure forms an end of the device, no end cap or closure is used, so that the second wall structure is unobstructed to provide a path for drug release.

In a preferred embodiment, the device is configured to release a therapeutically effective amount of the drug, where the rate of the release of the drug from the drug delivery device is zero order over at least 36 hours. In one embodiment, the rate of the release of the drug from the drug delivery device is essentially zero order over at least 7 days. In certain embodiments, the device is configured to begin release of the drug after a lag time, for example due to a void space in the inner washer. In certain embodiments, the lag time may at least about 30 minutes, from about 12 hours to about 24 hours, or up to about 2 days.

In preferred embodiments, the drugs are gemcitabine hydrochloride and trospium chloride. In one embodiment, at least 25 mg/day of gemcitabine is released over 7 days. In another embodiment, at least 1 mg/day of trospium chloride is released over 7 days to 3 months. In other embodiments, other drugs can be delivered with the devices described herein.

Other Aspects of the Implantable Drug Delivery Device

The devices and methods disclosed herein build upon those described in U.S. Pat. Nos. 8,182,464 and 8,343,516, as well as in U.S. Application Publication No. 2009/0149833 (MIT 12988); U.S. Application Publication No. 2010/0331770 (TB 101); U.S. Application Publication No. 2010/0060309 (TB 108); U.S. Application Publication No. 2011/0202036 (TB 107); U.S. Application Publication No. 2011/0152839 (TB 112); PCT/US11/46843, filed Aug. 5, 2011 (TB 113); U.S. application Ser. No. 13/267,560, filed Oct. 6, 2011 (TB 116); U.S. application Ser. No. 13/267,469, filed Oct. 6, 2011 (TB 117); and U.S. application Ser. No. 13/347,513, filed Jan. 10, 2012 (TB 120), each of which is incorporated herein by reference.

Figure 8A:
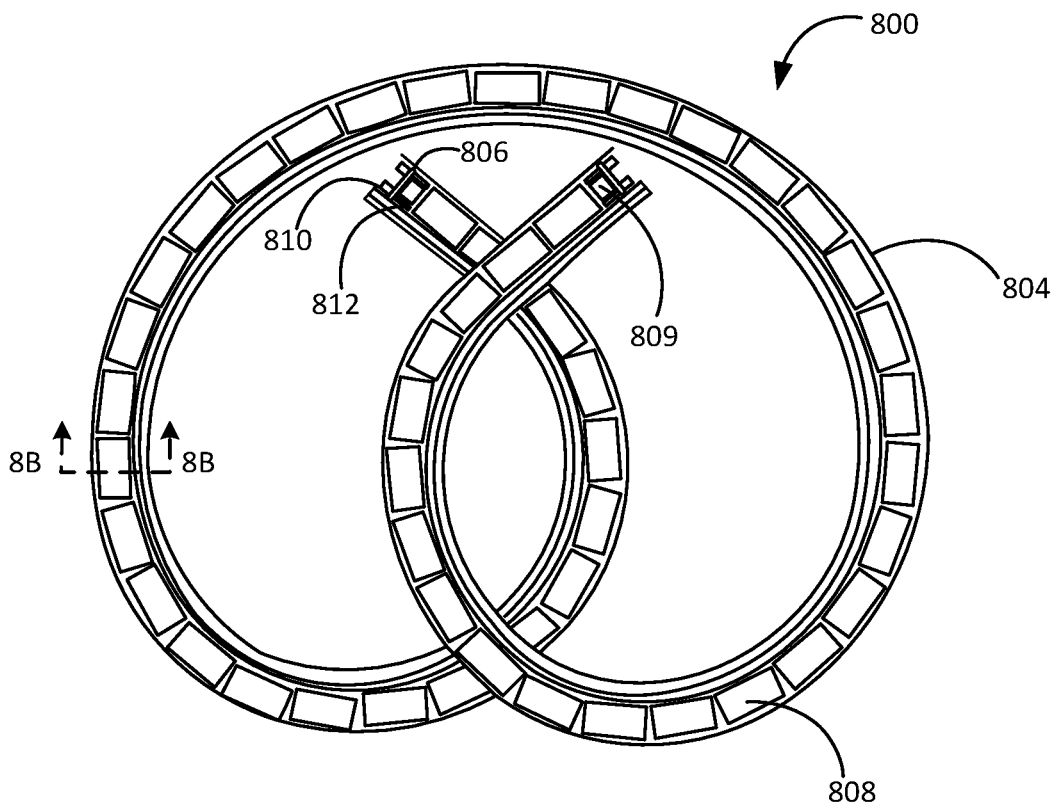
FIG. 8A is a plan view of one embodiment of an implantable drug delivery device wherein the second wall structure is an end wall.
Figure 8B:
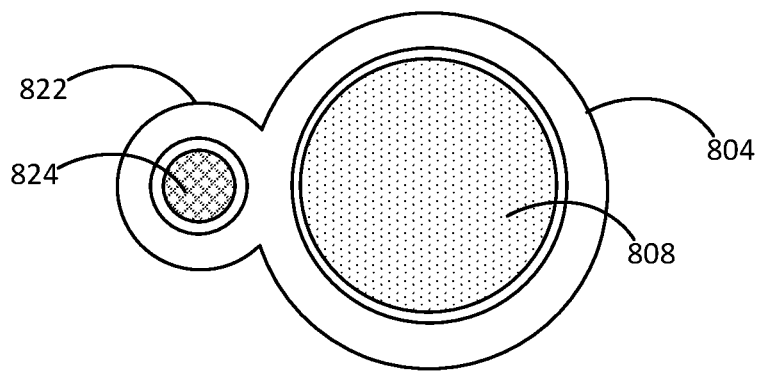
FIG. 8B is a cross-sectional view of the device of FIG. 8A.

In certain embodiments, the devices are configured for intravesical insertion and retention in a patient. For example, the devices can be elastically deformable between a relatively straightened shape suited for insertion through a lumen into a body cavity of a patient and a retention shape suited to retain the device within the body cavity, such as shown in FIG. 8A. When in the retention shape after deployment in the bladder, for example, the devices may resist excretion in response to the forces of urination or other forces. Since the devices are designed to be retained within a lumen or body cavity, they are capable of overcoming some of the deficiencies of conventional treatments, such as those related to the bladder. The devices described herein can be inserted once and release drug over a desired period of time without surgery or frequent interventions. The devices, as a result, may reduce the opportunity for infection and side effects, increase the amount of drug delivered locally or regionally to the bladder, or improve the quality of life of the patient during the treatment process. After drug release, the devices can be removed, for example by cystoscope and forceps, or be bioerodible, at least in part, to avoid a retrieval procedure.

The device may be loaded with at least one drug in the form of one or more solid drug units, such as tablets, capsules, or pellets. Providing one or more drugs in solid form to a patient is often advantageous. Solid drugs can provide a relatively large drug payload volume to total device volume and potentially enhance stability of the drugs during shipping, storage, before use, or before drug release. Solid drugs, however, should be solubilizable in vivo in order to diffuse into through the drug-permeable component and into the patient's surrounding tissues in a therapeutically effective amount.

Each drug reservoir lumen may hold one or several drug tablets or other solid drug units. In one embodiment, the device holds from about 10 to 100 cylindrical drug tablets, such as mini-tablets, among a number of discrete drug reservoir lumens. In certain embodiments, the mini-tablets may each have a diameter of about 1.0 to about 3.3 mm, such as about 1.5 to about 3.1 mm, and a length of about 1.5 to about 4.7 mm, such as about 2.0 to about 4.5 mm.

The devices may be inserted into a patient using a cystoscope or catheter. Typically, a cystoscope for an adult human has an outer diameter of about 5 mm and a working channel having an inner diameter of about 2.4 mm to about 2.6 mm. In embodiments, a cystoscope may have a working channel with a larger inner diameter, such as an inner diameter of 4 mm or more. Thus, the device may be relatively small in size. For example, when the device is elastically deformed to the relatively straightened shape, the device for an adult patient may have a total outer diameter that is less than about 2.6 mm, such as between about 2.0 mm and about 2.4 mm. For pediatric patients, the dimensions of the device are anticipated to be smaller, e.g., proportional for example based on the anatomical size differences and/or on the drug dosage differences between the adult and pediatric patients. In addition to permitting insertion, the relatively small size of the device may also reduce patient discomfort and trauma to the bladder.

In one embodiment, the overall configuration of the device promotes in vivo tolerability for most patients. In a particular embodiment, the device is configured for tolerability based on bladder characteristics and design considerations described in U.S. Application Publication No. 2011/0152839 (TB 112), which is incorporated herein by reference.

Within the three-dimensional space occupied by the device in the retention shape, the maximum dimension of the device in any direction preferably is less than 10 cm, the approximate diameter of the bladder when filled. In some embodiments, the maximum dimension of the device in any direction may be less than about 9 cm, such as about 8 cm, 7 cm, 6 cm, 5 cm, 4.5 cm, 4 cm, 3.5 cm, 3 cm, 2.5 or smaller.

In particular embodiments, the maximum dimension of the device in any direction is less than about 7 cm, such as about 6 cm, 5 cm, 4.5 cm, 4 cm, 3.5 cm, 3 cm, 2.5 cm or smaller. In preferred embodiments, the maximum dimension of the device in any direction is less than about 6 cm, such as about 5 cm, 4.5 cm, 4 cm, 3.5 cm, 3 cm, 2.5 cm or smaller. More particularly, the three-dimension space occupied by the device is defined by three perpendicular directions. Along one of these directions the device has its maximum dimension, and along the two other directions the device may have smaller dimensions. For example, the smaller dimensions in the two other directions may be less than about 4 cm, such as about 3.5 cm, 3 cm, 2.5 cm or less. In a preferred embodiment, the device has a dimension in at least one of these directions that is less than 3 cm.

In some embodiments, the device may have a different dimension in at least two of the three directions, and in some cases in each of the three directions, so that the device is non-uniform in shape. Due to the non-uniform shape, the device may be able to achieve an orientation of reduced compression in the empty bladder, which also is non-uniform in shape. In other words, a particular orientation of the device in the empty bladder may allow the device to exert less contact pressure against the bladder wall, making the device more tolerable for the patient.

The overall shape of the device may enable the device to reorient itself within the bladder to reduce its engagement or contact with the bladder wall. For example, the overall exterior shape of the device may be curved, and all or a majority of the exterior or exposed surfaces of the device may be substantially rounded. The device also may be substantially devoid of sharp edges, and is exterior surfaces may be formed from a material that experiences reduced frictional engagement with the bladder wall. Such a configuration may enable the device to reposition itself within the empty bladder so that the device applies lower contact pressures to the bladder wall. In other words, the device may slip or roll against the bladder wall into a lower energy position, meaning a position in which the device experiences less compression.

In one embodiment, device is generally planar in shape even though the device occupies three-dimensional space. Such a device may define a minor axis, about which the device is substantially symmetrical, and a major axis that is substantially perpendicular to the minor axis. The device may have a maximum dimension in the direction of the major axis that does not exceed about 6 cm, and in particular embodiments is less than 5 cm, such as about 4.5 cm, about 4 cm, about 3.5 cm, about 3 cm, or smaller. The device may have a maximum dimension in the direction of the minor axis that does not exceed about 4.5 cm, and in particular embodiments is less than 4 cm, such as about 3.5 cm, about 3 cm, or smaller. The device is curved about substantially its entire exterior perimeter in both a major cross-sectional plane and a minor cross-sectional plane. In other words, the overall exterior shape of the device is curved and the cross-sectional shape of the device is rounded. Thus, the device is substantially devoid of edges, except for edges on the two flat ends, which are completely protected within the interior of the device when the device lies in a plane. These characteristics enable the device to reorient itself into a position of reduced compression when in the empty bladder.

The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder.

The device also may be configured to facilitate buoyancy, such as with the use of low density materials of construction for the housing components and/or by incorporating gas or gas generating materials into the housing, as described for example in U.S. Application Publication No. 2012/0089121 (TB 116), which is incorporated herein by reference. In general, the device in the dry and drug-loaded state may have a density in the range of about 0.5 g/mL to about 1.5 g/mL, such as between about 0.7 g/mL to about 1.3 g/mL. In some embodiments, the device in the dry and drug-loaded state has a density that is less than 1 g/mL.

The implantable drug delivery device can be made to be completely or partially bioerodible so that no explanation, or retrieval, of the device is required following release of the drug formulation. In some embodiments, the device is partially bioerodible so that the device, upon partial erosion, breaks into non-erodible pieces small enough to be excreted from the bladder. As used herein, the term "bioerodible" means that the device, or part thereof, degrades in vivo by dissolution, enzymatic hydrolysis, erosion, resorption, or combinations thereof. In one embodiment, this degradation occurs at a time that does not interfere with the intended kinetics of release of the drug from the device. For example, substantial erosion of the device may not occur until after the drug formulation is substantially or completely released. In another embodiment, the device is erodible and the release of the drug formulation is controlled at least in part by the degradation or erosion characteristics of the erodible device body. The devices described herein may be designed to conform with the characteristics of those described in U.S. Application Publication No. 2012/0089122 (TB 117), which is incorporated herein by reference.

Useful biocompatible erodible materials of construction are known in the art. Examples of suitable such materials include synthetic polymers selected from poly(amides), poly (esters), poly(ester amides), poly(anhydrides), poly(orthoesters), polyphosphazenes, pseudo poly(amino acids), poly (glycerol-sebacate)(PGS), copolymers thereof, and mixtures thereof. In one embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly (octanediol citrate) (POC). PC-based polymers may require additional cross-linking agents such as lysine diisocyanate or 2,2-bis($\varepsilon$-caprolacton-4-yl)propane to obtain elastomeric properties.

Alternatively, the implantable drug delivery device may be at least partially non-bioerodible. It may be formed of medical grade silicone tubing, as known in the art. Other examples of suitable non-resorbable materials include synthetic polymers selected from ethylene vinyl acetate (EVA), poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene), polyamide and other fluorinated polymers, poly(siloxanes), copolymers thereof, and combinations thereof. Following release of the drug formulation, the device and/or the retention frame may be removed substantially intact or in multiple pieces.

The drug delivery device may be sterilized before being inserted into a patient. In one embodiment, the device is sterilized using a suitable process such as gamma irradiation or ethylene oxide sterilization, although other sterilization processes may be used.

Retention of the Device in a Body Cavity

The devices described herein are elastically deformable between a relatively straightened shape suited for insertion through a lumen into the bladder (or other body cavity) of a patient and a retention shape suited to retain the device within the bladder (or other body cavity). In certain embodiments, the drug delivery device may naturally assume the retention shape and may be deformed, either manually or with the aid of an external apparatus, into the relatively straightened shape for insertion into the body. Once deployed the device may spontaneously or naturally return to the initial, retention shape for retention in the body.

For the purposes of this disclosure, the term "retention shape" generally denotes any shape suited for retaining the device in the intended implantation location, including, but not limited to, a coiled or "pretzel" shape, such as shown in FIG. 8A, which is suited for retaining the device in the bladder. Similarly, the term "relatively straightened shape" generally denotes any shape suited for deploying the drug delivery device into the body, including, but not limited to, a linear or elongated shape, which is suited for deploying the device through the working channel of catheter, cystoscope, or other deployment instrument positioned in a lumen of the body, such as the urethra.

In some embodiments, the drug delivery devices do not need a retention frame to be elastically deformable between a relatively straightened shape and a retention shape. In these embodiments, the material from which the housing is formed makes the device capable of being elastically deformed between the two shapes.

In other embodiments, the drug delivery devices include a retention frame that is associated with the housing. The properties of the retention frame cause the device to function as a spring, deforming in response to a compressive load but spontaneously returning to its initial shape once the load is removed.

As shown in FIGS. 8A-8B, 9, 11A-11B, and 12A-12C, the housing may include one or more retention frame lumens 822, 922, 1122, and 1222, respectively, through which at least a portion of a retention frame 824, 924, 1124, 1224, respectively, is threaded. In some embodiments, the housing does not include a separate retention frame lumen, and the retention frame is affixed to the housing any other means, such as an adhesive, or the retention frame and drug occupy the same lumen.

In certain embodiments, the retention frame, like the devices themselves, may naturally assume the retention shape, may be deformed into the relatively straightened shape, and may spontaneously return to the retention shape upon insertion into the body. The retention frame in the retention shape may be shaped for retention in a body cavity, and the retention frame in the relatively straightened shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In a preferred embodiment, the device is elastically deformable between a relatively straightened shape suited for insertion through a catheter or cystoscope extending through a patient's urethra of a patient and a curved or coiled shape suited to retain the device within the bladder (i.e., to prevent its expulsion from the bladder during urination) following release of the device from the end of the catheter or cystoscope. In a particular configuration of this embodiment, the device has an elastic wire or strip serving as the retention frame, and the elastic wire or strip acts as a spring to maintain the device in the curved or coiled shape in the absence of a compressive load on the device and when the device is under compression from the bladder walls during urination or other contraction of the patient's detrusor muscle.

In certain embodiments, the retention frame includes or consists of an elastic wire or an elastic strip. In one embodiment, the elastic wire may comprise a biocompatible shape-memory material or a biodegradable shape memory polymer as known in the art. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

In some embodiments, the retention frame lumen may include the retention frame and a filling material, such as a silicone adhesive, such as MED3-4213 by Nusil Technology LLC, although other filling materials may be used. The filling material is optional and may be omitted; however, its inclusion may fill the void in the retention frame lumen about the retention frame and may reduce the tendency of the drug reservoir lumen to stretch along, or twist or rotate about, the retention frame, while maintaining the drug reservoir lumen in a selected orientation with reference to the retention frame.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame (or the housing itself in embodiments without a retention frame) comprises a shape-memory material, the material used to form the frame may "memorize" and spontaneously assume the retention shape upon the application of heat to the device, such as when exposed to body temperatures upon entering the bladder. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

The retention frame may have a two-dimensional structure that is confined to a plane, a three-dimensional structure, such as a structure that occupies the interior of a spheroid, or some combination thereof. The frames may comprise one or more loops, curls, or sub-circles, connected either linearly or radially, turning in the same or in alternating directions, and overlapping or not overlapping. The frames may comprise one or more circles or ovals arranged in a two-dimensional or a three-dimensional configuration, the circles or ovals may be either closed or opened, having the same or different sizes, overlapping or not overlapping, and joined together at one or more connecting points. The retention frame portion also may be a three-dimensional structure that is shaped to occupy or wind about a spheroid-shaped space, such as a spherical space, a space having a prorate spheroid shape, or a space having an oblate spheroid shape. Retention frame portions may be shaped to occupy or wind about a spherical space. The retention frame portion may generally take the shape of two intersecting circles lying in different planes, two intersecting circles lying in different planes with inwardly curled ends, three intersecting circles lying in different planes, or a spherical spiral. In each of these examples, the retention frame portion can be stretched to the linear shape for deployment through a deployment instrument. The retention frame portion may wind about or through the spherical space, or other spheroid-shaped space, in a variety of other manners. One or both of the retention frame and retention frame lumen may be omitted, in which case the housing itself may assume or may be deformed into any retention shape described herein. Examples of alternative configurations are described in the U.S. Patent Applications incorporated by reference herein.

The Drug Formulation and Solid Drug Tablets

Generally, a drug formulation is formed into solid drug units that are loaded into the device housing. Each of the solid drug units is a solid, discrete object that substantially retains a selectively imparted shape (at the temperature and pressure conditions to which the delivery device normally will be exposed during assembly, storage, and handling before implantation). The drug units may be in the form of tablets, capsules, pellets, or beads, although other configurations are possible.

The solid drug units can be formed using a stable and scalable manufacturing process. Particularly, the drug tablets are sized and shaped for loading into and efficiently storing the tablets in a housing of a drug delivery device that can be deployed into the bladder or another cavity, lumen, or tissue site in a patient in a minimally invasive manner.

The solid drug units may be made by a direct powder compaction or tabletting process, a molding process, or other processes known in the pharmaceutical arts. Suitable drug tablet forming methods are described in U.S. Application Publication No. 2010/0330149 (TB 102), which is incorporated herein by reference. The drug formulation also may be loaded into the device housing in workable form and may cure therein. For example, in embodiments in which the drug formulation is configured to be melted and solidified, the drug formulation can be melted, injected into the device housing in melted form and then solidified. The drug formulation also may be extruded with the device housing, may cure within the housing, and subsequently may be cut in spaced positions along the length of the housing to form segments with exposed surface areas of drug.

The solid drug unit includes a drug formulation, which includes a drug content and may include an excipient content. In a preferred embodiment, the drug content includes one or more drugs, or active pharmaceutical ingredients (API), while the excipient content includes one or more pharmaceutically acceptable excipients. The drug formulation can include essentially any therapeutic, prophylactic, or diagnostic agent, such as one that would be useful to deliver locally to a body cavity or lumen or regionally about the body cavity or lumen. The drug formulation may consist only of the API, or one or more excipients may be included. As used herein, the term "drug" with reference to any specific drug described herein includes its alternative forms, such as salt forms, free acid forms, free base forms, and hydrates. The term "excipient" is known in the art, and representative examples of excipients useful in the present drug units may include ingredients such as binders, lubricants, glidants, disintegrants, colors, fillers, diluents, coatings, or preservatives, as well as other non-active ingredients to facilitate manufacturing, stability, dispersibility, wettability, and/or release kinetics of the drug or administering the drug unit. The drug may be small molecule, macromolecule, biologic, or metabolite, among other forms/types of active ingredients.

In order to maximize the amount of drug that can be stored in and released from a given drug delivery device of a selected (small) size, the drug unit preferably comprises a high weight fraction of drug or API, with a reduced or low weight fraction of excipients as are required for solid drug unit manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a solid drug unit that has 90% by weight of a drug in salt form may include less than 90% by weight of that drug in free base form.

In one embodiment, the solid drug unit is more than 50% by weight drug. In another embodiment, 75% or more of the weight of the solid drug unit is drug, with the remainder of the weight comprising excipients, such as lubricants and binders that facilitate making the solid drug unit. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the solid drug unit. In some cases, the drug content comprises about 75% or more of the weight of the solid drug unit. More particularly, the drug content may comprise about 80% or more of the weight of the drug tablet. For example, the drug content may comprise between about 85% and about 99.9% of the weight of the solid drug unit. In some embodiments, the excipient content can be omitted completely.

In one embodiment, the drug and excipients are selected and the solid drug unit formulated to be water soluble, so that the solid drug units can be solubilized when the device is located within the bladder, to release the solubilized drug.

The individual solid drug units may have essentially any selected shape and dimension that fits within the devices described herein. In one embodiment, the solid drug units are sized and shaped such that the drug reservoir lumens in the housings are substantially filled by a select number of solid drug units. Each solid drug unit may have a cross-sectional shape that substantially corresponds to a cross-sectional shape of the drug reservoir lumen of a particular housing. For example, the drug units may be substantially cylindrical in shape for positioning in a substantially cylindrical drug reservoir lumen. Once loaded, the solid drug units can, in some embodiments, substantially fill the drug reservoir lumens, forming the drug housing portion.

In one embodiment, the solid drug units are shaped to align in a row when the device is in its deployment configuration. For example, each solid drug unit may have a cross-sectional shape that corresponds to the cross-sectional shape of the drug reservoir lumens in the housing, and each solid drug unit may have end face shapes that correspond to the end faces of adjacent solid drug units. The interstices or breaks between solid drug units can accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

In embodiments in which the solid drug units are designed for insertion or implantation in a lumen or cavity in the body, such as the bladder, via a drug delivery device, the drug units may be "mini-tablets" that are suitably sized and shaped for insertion through a natural lumen of the body, such as the urethra. For the purpose of this disclosure, the term "mini-tablet" generally indicates a solid drug unit that is substantially cylindrical in shape, having end faces and a side face that is substantially cylindrical. The mini-tablet has a diameter, extending along the end face, in the range of about 1.0 to about 3.2 mm, such as between about 1.5 and about 3.1 mm. The mini-tablet has a length, extending along the side face, in the range of about 1.7 mm to about 4.8 mm, such as between about 2.0 mm and about 4.5 mm. The friability of the tablet may be less than about 2%. Embodiments of solid drug units and systems and methods of making the same are further described below with reference to U.S. Patent Applications incorporated by reference herein.

In one embodiment, the drug formulation is in a solid form. In another embodiment, the drug formulation is in semi-solid form, such as an emulsion or suspension; a gel or a paste. For example, the drug formulation may be a highly viscous emulsion or suspension. As used herein, the solid form includes semi-solid forms unless otherwise indicated. In one embodiment, the drug formulation is in a liquid form.

The drug may be a low solubility drug. As used herein, the term "low solubility" refers to a drug having a solubility from about 0.01 mg/mL to about 10 mg/mL water at 37° C. In other embodiments, the drug is a high solubility drug. As used herein, the term "high solubility" refers to a drug having a solubility above about 10 mg/mL water at 37° C. For example, the approximate solubilities of certain drug formulations are: trospium chloride: 500 mg/mL; lidocaine HCl: 680 mg/mL; lidocaine base: 8 mg/mL, gemcitabine HCl: 80 mg/mL; gemcitabine base: 15 mg/mL; oxybutynin HCl: 50 mg/mL; oxybutynin base: 0.012 mg/mL; and tolterodine tartrate: 12 mg/mL.

In one embodiment, the drug delivery device is used to treat renal or urinary tract cancer, such as bladder cancer and prostate cancer. Drugs that may be used include antiproliferative agents, cytotoxic agents, chemotherapeutic agents, or combinations thereof. Representative examples of drugs which may be suitable for the treatment of urinary tract cancer include *Bacillus* Calmette Guerin (BCG) vaccine, docetaxel, cisplatin, doxorubicin, valrubicin, gemcitabine, mycobacterial cell wall-DNA complex (MCC), methotrexate, vinblastine, thiotepa, mitomycin (e.g., mitomycin C), fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may comprise a monoclonal antibody, a TNF inhibitor, an antileukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

In one embodiment, the devices described herein are loaded with an anesthetic agent, analgesic agent, and combinations thereof. The anesthetic agent may be an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, mepryl-caine, metabutoxycaine, orthocaine, piperocaine, procaine, proparacaine, propoxycaine, proxymetacaine, risocaine, and tetracaine. These anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, and naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, cyclosporine, or combinations thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin. Evidence suggests that the bladder expresses nerve growth factor (NGF) locally, since exogenously delivered NGF into the bladder induces bladder hyperactivity and increases the excitability of dissociated bladder afferent neurons (Nature Rev Neurosci 2008; 9:453-66). Accordingly, it would be advantageous to locally deliver a MAB or other agent against NGF using the described delivery devices, significantly reducing the total dose needed for therapeutic efficacy. Evidence also suggests that binding of the alpha-2-delta unit of voltage-sensitive calcium channels, such as with gabepentin, may be effective in the treatment of diseases of neuropathic pain such as fibromyalgia and that there may be common mechanisms between IC and diseases of neuropathic pain (See Tech Urol. 2001 March, 7(1):47-49). Accordingly, it would be advantageous to locally deliver a calcium channel alpha-2-delta modulator, such as PD-299685 or gabepentin, using the described delivery devices, minimizing does-related systemic toxicities in the treatment of IC.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as EGF-dextran, HPC-doxorubicin, IL-12, IFN-α2b, IFN-γ, α-lactalbumin, p53 adenovector, TNFα; combinations, such as Epirubicin+BCG, IFN+farmarubicin, Doxorubicin +5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

The drug delivery device can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopres sin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In still another embodiment, the present intravesical drug delivery device is used to treat infections involving the bladder, the prostate, the kidney, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the drug delivery device is used to treat fibrosis of a genitourinary site, such as the bladder or uterus. Representative examples of drugs for the treatment of fibroids include pentoxphylline (xanthine analogue), anti-TNF, antiTGF agents, GnRH analogues, exogenous progestins, antiprogestins, selective estrogen receptor modulators, danazol and NSAIDs.

The implantable drug delivery device also may be used to treat spastic or flaccid neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants); drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

In certain embodiments, the drug is a steroid, such as triamcinolone, budesonide, or prednisolone.

In certain embodiments, the drug is lidocaine, gemcitabine, docetaxel, carboplatin, cisplatin, oxaliplatin, trospium, tolterodine, oxybutynin, or mitomycin C.

Other Device Features

The devices described herein may include a radio-opaque portion or structure to facilitate detection or viewing (e.g., by X-ray imaging or fluoroscopy) of the device by a medical practitioner as part of the implantation or retrieval procedure. In one embodiment, the housing is constructed of a material that includes a radio-opaque filler material, such as barium sulfate or another radio-opaque material known in the art. Some housings may be made radio-opaque by blending radio-opaque fillers, such as barium sulfate or another suitable material, during the processing of the material from which the housing is formed. The radio-opaque material may be associated with the retention frame in those embodiments that include a retention frame. Ultrasound imaging or fluoroscopy may be used to image the device in vivo.

The housing of the implantable drug delivery device may further include a retrieval feature, such as a string, a loop, or other structure that facilitates removal of the device from the body cavity, for example for removal of a non-resorbable device body following release of the drug formulation from the solid drug units. In one case, the device may be removed from the bladder by engaging the string to pull the device through the urethra. The device may be configured to assume a relatively narrow or linear shape when pulling the device by the retrieval feature into the lumen of a catheter or cystoscope or into the urethra.

Methods for Drug Delivery

The devices and methods disclosed herein may be adapted for use in humans, whether male or female, adult or child, or for use in animals, such as for veterinary or livestock applications. Accordingly, the term "patient" may refer to a human or other mammalian subject.

In certain embodiments, a method of providing controlled release of drug to a patient includes (i) deploying a drug delivery device in the patient, the device comprising a closed drug reservoir lumen bounded by a first wall structure and a hydrophilic second wall structure; and (ii) releasing a drug from the drug reservoir lumen via diffusion through the second wall structure, wherein the first wall structure is impermeable to the drug, and the second wall structure is permeable to the drug. In one embodiment, the first wall structure is a cylindrical tube and the second wall structure is an end wall disposed at at least one end of the cylindrical tube, or the first wall structure and the second wall structure are adjacent one another and together form a cylindrical tube. For example, the device may include any features, or combinations of features, described herein.

The device may be implanted non-surgically and may deliver drug for several days, weeks, months, or more after the implantation procedure has ended. In one embodiment, implanting the drug delivery device in the patient includes inserting the device into a body cavity or lumen of the patient via a deployment instrument. For example, the device may be deployed through a deployment instrument, such as a catheter or cystoscope, positioned in a natural lumen of the body, such as the urethra, or into a body cavity, such as the bladder. The deployment instrument typically is removed from the body lumen while the drug delivery device remains in the bladder or other body cavity for a prescribed treatment period.

The device, in some embodiments, may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one example, the device is implanted by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. The deployment instrument may be any suitable lumen device, such as a catheter, e.g., a urethral catheter, or cystoscope. These terms are used interchangeably herein, unless otherwise expressly indicated. The deployment instrument may be a commercially available device or a device specially adapted for the present drug delivery devices. In one embodiment, deploying the drug delivery device in the patient includes (i) elastically deforming the device into a relatively straightened shape; (ii) inserting the device through the patient's urethra; and (iii) releasing the device into the patient's bladder such that it assumes a retention shape suited to retain the device within the bladder.

The drug delivery device may be passed through the deployment instrument, driven by a stylet or flow of lubricant or other fluid, for example, until the drug delivery device exits a lumen of the instrument as passes into the bladder. Thus, the device may be implanted into the bladder of a male or female human patient in need of treatment, either adult or child.

Once deployed in vivo, the device subsequently may release one or more drugs for the treatment of one or more conditions, locally to one or more tissues at the deployment site and/or regionally to other tissues distal from the deployment site. The release may be controlled and may release the drug in an effective amount over an extended period. Thereafter, the device may be removed, resorbed, excreted, or some combination thereof. In certain embodiments, the device resides in the bladder releasing the drug over a predetermined period, such as two weeks, three weeks, four weeks, a month, or more.

Once implanted, the device may provide extended, continuous, intermittent, or periodic release of a desired quantity of drug over a desired, predetermined period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated. In one embodiment, a rate of release of the drug from the drug delivery device is zero order over at least 36 hours. In one embodiment, a rate of the release of the drug from the drug delivery device is essentially zero order over at least 7 days.

In certain embodiments, elution of drug from the device occurs following dissolution of the drug within the device. Bodily fluid enters the device, contacts the drug and solubilizes the drug, and thereafter the dissolved drug diffuses from the device. For example, the drug may be solubilized upon contact with urine in cases in which the device is implanted in the bladder. In one embodiment, releasing the drug from the device includes solubilizing the drug with water imbibed through the second wall structure, or both the first and second wall structures.

The device may be used to treat interstitial cystitis, radiation cystitis, pelvic pain, bladder inflammation, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may release drug locally to the bladder and regionally to other sites near the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including the kidneys, urethra, ureters, penis, testes, seminal vesicles, vas deferens, ejaculatory ducts, prostate, vagina, uterus, ovaries, or fallopian tubes, among others or combinations thereof. For example, the drug delivery device may be used in the treatment of kidney stones or fibrosis, erectile dysfunction, among other diseases, disorders, and conditions.

In one embodiment, the device may have two payloads of drug that are released at different times. The first payload may be adapted for relatively quick release, while the second payload may be adapted for more continuous release.

Subsequently, the device may be retrieved from the body, such as in cases in which the device is non-resorbable or otherwise needs to be removed. Retrieval devices for this purpose are known in the art or can be specially produced. The device also may be completely or partially bioerodible, resorbable, or biodegradable, such that retrieval is unnecessary, as either the entire device is resorbed or the device sufficiently degrades for expulsion, for example, from the bladder during urination. The device may not be retrieved or resorbed until some of the drug, or preferably most or all of the drug, has been released. If needed, a new drug-loaded device may subsequently be implanted, during the same procedure as the retrieval or at a later time.

The present invention may be further understood with reference to the following non-limiting examples.

Example 1

Pouches formed of Tecophilic™ film and loaded with gemcitabine (GEM) were tested in vitro for drug permeation. The effect of gamma irradiation on these pouches was also studied.

The pouches were made of HP-93A-100 and HP-60D-60 films with thickness of 0.5 mm (films provided by Lubrizol) (http://www.lubrizol.com/Medical/Products/Tecophilic.html). These thermoplastic polyurethanes (TPUs) were selected for their biocompatibility and ability to absorb equilibrium water content up to 100% of the weight of dry resin, as well as other properties. The material properties of the film materials used are given below in Table 1.

TABLE 1

Tecophilic ™ HP-93A-100 and HP-60D-60 Film Material Properties

|  | ASTM | HP-60D-60 | HP-93A100 |
|---|---|---|---|
| Durometer (Shore Hardness) | D2240 | 41D | 83A |
| Specific Gravity | D792 | 1.15 | 1.13 |
| Flexural Modulus (psi) | D790 | 4000 | 2900 |
| Ultimate Tensile (psi) D412 |  |  |  |
| Dry |  | 8300 | 2200 |
| Wet |  | 3100 | 1400 |
| Ultimate Elongation | D412 |  |  |
| Dry |  | 500 | 1040 |
| Wet |  | 300 | 620 |
| Water Absorption (%) |  | 60 | 100 |

Each pouch was made out of 2 films which were heat-sealed at all four edges of each pouch after loading each pouch with a single tablet of gemcitabine HCl or base formulated as follows:

(1) Gemcitabine HCl: 89% GEM HCl, 10% Isomalt, 1% Lubritab (water insoluble), or (2) Gemcitabine Base: 90% GEM Base, 5% PEG 8k, 5% PVP.

Some of the pouches were gamma irradiated (25 kGy). The pouches were then placed into 21 mL DI water at 37° C. Thereafter, at each time point, 5× inversion, 1 mL sample was taken out followed by a 1 mL DI water refill.

The cumulative amounts (in mg FBE or Free Base Equivalent) and percent amounts of drug released are illustrated in FIGS. 13-24. The results show that gemcitabine, in either HCl or base form, permeated 0.5 mm Tecophilic™ film. Faster release was observed with HP-93A-100 (lower durometer) than with HP-60D-60 (higher durometer). Gemcitabine HCl (higher solubility) was released faster than gemcitabine base (lower solubility). No negative effect from the gamma irradiation was observed.

Example 1A

Pouches constructed as in Example 1 were made, except each was loaded with 1 gemcitabine (GEM) HCl tablet and 4 tablets of urea. The pouches were then placed into 21 mL DI water at 37° C. Thereafter, at each time point, 5× inversion, 1 mL sample was taken out followed by a 1 mL DI water refill.

The percent amounts of drug and urea released from the samples are illustrated in Tables 2-4 below. The results show that the gemcitabine and urea permeated 0.5 mm Tecophilic™ film in one day. Faster release was observed with HP-93A-100 (lower durometer) than with HP-60D-60 (higher durometer).

TABLE 2

Sample Compositions

| Sample | GEM FBE (mg) | Urea (mg) | Sealed Area (cm × cm) |
|---|---|---|---|
| HP-60D-60 (1) | 21 | 129 | 1.7 × 2.6 |
| HP-60D-60 (2) | 20 | 129 | 1.6 × 2.5 |
| HP-93A-100 (1) | 21 | 134 | 1.6 × 2.9 |
| HP-93A-100 (2) | 22 | 120 | 1.5 × 2.7 |

TABLE 3

Percent Amount Gemcitabine Released (%) at Various Times

| Sample | 2 hour | 1 day | 2 day |
|---|---|---|---|
| HP-60D-60 (1) | 0 | 95 | 96 |
| HP-60D-60 (2) | 0 | 92 | 96 |
| HP-93A-100 (1) | 1 | 91 | 92 |
| HP-93A-100 (2) | 4 | 93 | 94 |

TABLE 4

Percent Amount Urea Released (%) as Various Times

| Sample | 2 hour | 1 day | 2 day |
|---|---|---|---|
| HP-60D-60 (1) | 13 | 99 | 100 |
| HP-60D-60 (2) | 12 | 99 | 100 |
| HP-93A-100 (1) | 61 | 98 | 99 |
| HP-93A-100 (2) | 62 | 99 | 99 |

Example 1B

Squares (0.5 inch×0.5 in) of HP-93A-100 and HP-60D-60 films with thickness of 0.020" (films provided by Lubrizol) were cut and placed into 50 mL DI water at 37° C. The mass of each film was measured at T=0 and again at T=1 day, in order to measure water absorption of the film. The areas of each film were also measured at T=0 and again at T=1 day, in order to measure the increase in area of the film due to water absorption. The results are shown in Table 5 below The HP-93A-100 (lower durometer) was observed to increase in mass and water-swell, or expand, in area more than the HP-60D-60 (higher durometer) did.

TABLE 5

Mass and Area Measurements of Dry and Wet Samples

| Sample | Dry Mass (mg) | Wet Mass (mg) | % Mass Increase | Dry Area (cm$^2$) | Wet Area (cm$^2$) | % Area Increase |
|---|---|---|---|---|---|---|
| HP-93A-100 (1) | 89 | 162 | 82 | 1.6 | 2.6 | 64 |
| HP-93A-100 (2) | 88 | 160 | 82 | 1.6 | 2.6 | 64 |
| HP-60D-60 (1) | 80 | 117 | 46 | 1.6 | 2.0 | 25 |
| HP-60D-60 (2) | 91 | 135 | 49 | 1.6 | 2.0 | 25 |

Example 2

Figure 25:
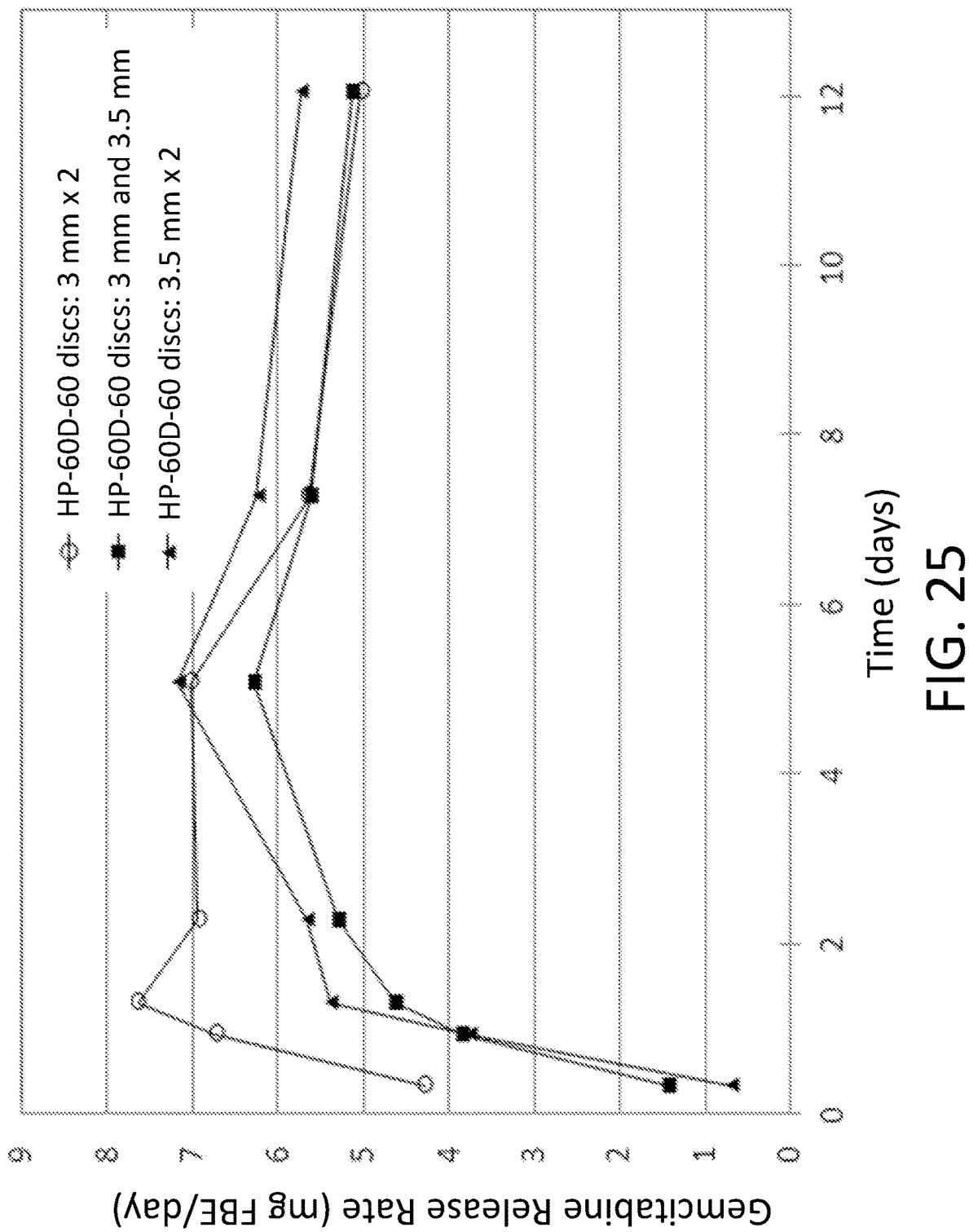
FIG. 25 is a graph showing the release rate of gemcitabine from devices having drug permeable end wall disks of varying size, over time.

A silicone tube made of MED-4750 (Nusil) had the dimensions of 2.64 mm ID and 0.20 mm wall thickness. Multiple gemcitabine HCl tablets with 2.6 mm OD were loaded into the silicone tube with a total gemcitabine HCl payload of approximately 380 mg. Each end of the tablets drug core had a 0.5 mm thickness disk made of HP-60D-60 (Tecophilic™ Thermoplastic Polyurethanes). The diameters of the disks are shown in FIG. 25. The disks were oversized compared with silicone tube ID, and so they were frictionally fit into the tube. The layout of each device in the silicone tube was: Disk—Tablets—Disk. Three devices were built and placed in deionized water at 37° C. for in vitro release experiment. Results are shown in FIG. 25. Y-axis indicates gemcitabine release rate, and the unit is mg FBE (Free Base Equivalent) per day.

Example 3

Figure 26:
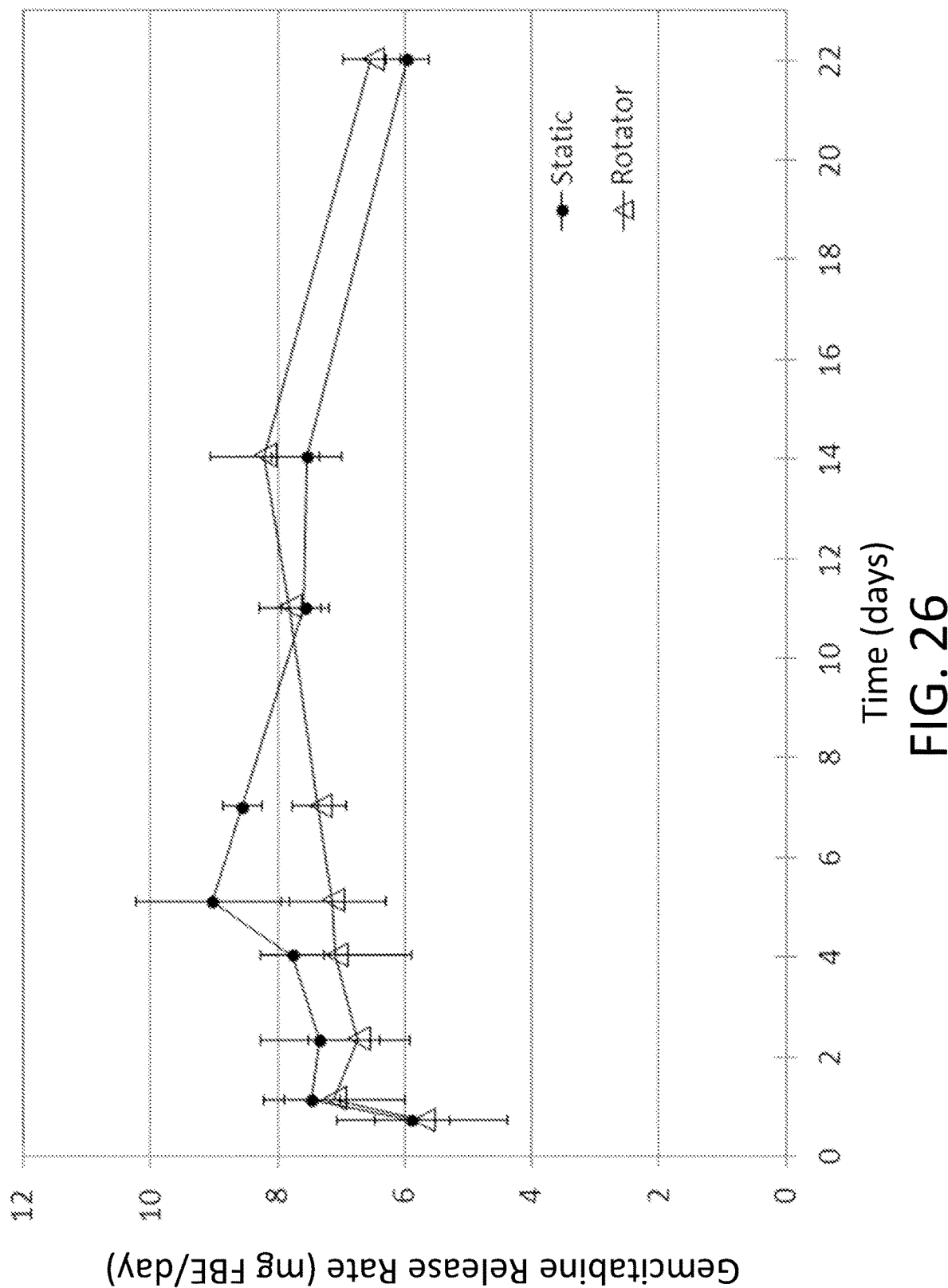
FIG. 26 is a graph showing the release rate of gemcitabine from static and rotated devices having drug permeable end wall disks, over time.

A silicone tube made of MED-4750 (Nusil) had dimensions of 2.64 mm ID and 0.20 mm wall thickness. Multiple gemcitabine HCl tablets with 2.6 mm OD were loaded into the silicone tube with a total gemcitabine HCl payload of approximately 200 mg. Each device had a disk made of HP-93A-100 (Tecophilic™ Thermoplastic Polyurethanes) at each end of the tablets drug core. The dimensions of each disk were approximately 0.5 mm thickness and 3.0 mm OD. The OD (3.0 mm) of the disks was larger than the silicone tube ID (2.64 mm), and so the disks were frictionally fit in the silicone tube. In addition, there was a silicone washer, made of MED-4780 (Nusil), located next to each disk with silicone adhesive (MED3-4213) applied around the washer, to stabilize the outward migration of the disk. The silicone washer had the dimensions of ID, OD, and the length of approximately 2.5 mm, 3.2 mm, and 2 mm, respectively. The layout of each device in the silicone tube was: Silicone Washer—Disk—Tablets—Disk—Silicone Washer. Six devices were built and placed in deionized water at 37° C. for in vitro release experiment. They were divided into two groups. In one group, the releasing jars were rotated in the rotator at 4 rpm (labeled 'Rotator') as opposed to the other group (labeled 'Static'). Results are shown in FIG. 26. Each error bar shown below is standard deviation around the mean (n=3 for each group). Y-axis indicates gemcitabine release rate, and the unit is mg FBE (Free Base Equivalent) per day.

Example 4

Figure 27:
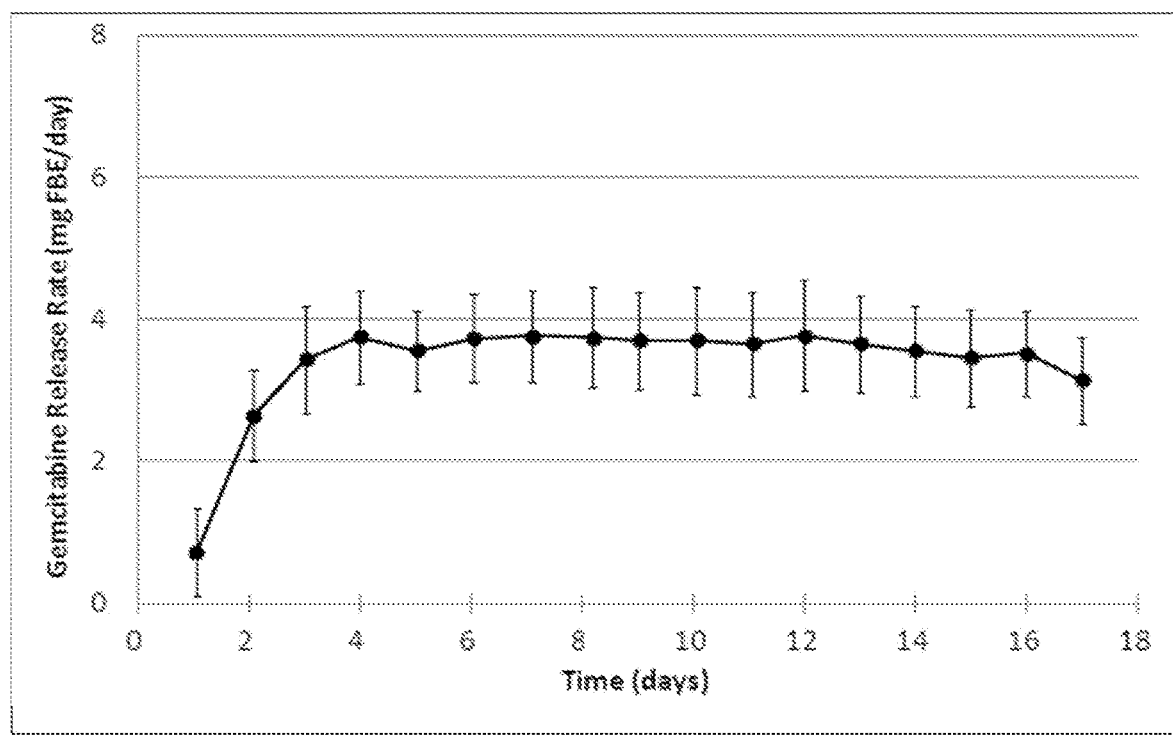
FIG. 27 is a graph showing the release rate of gemcitabine from a device having a drug permeable end wall disk at one end, over time.
Figure 28:
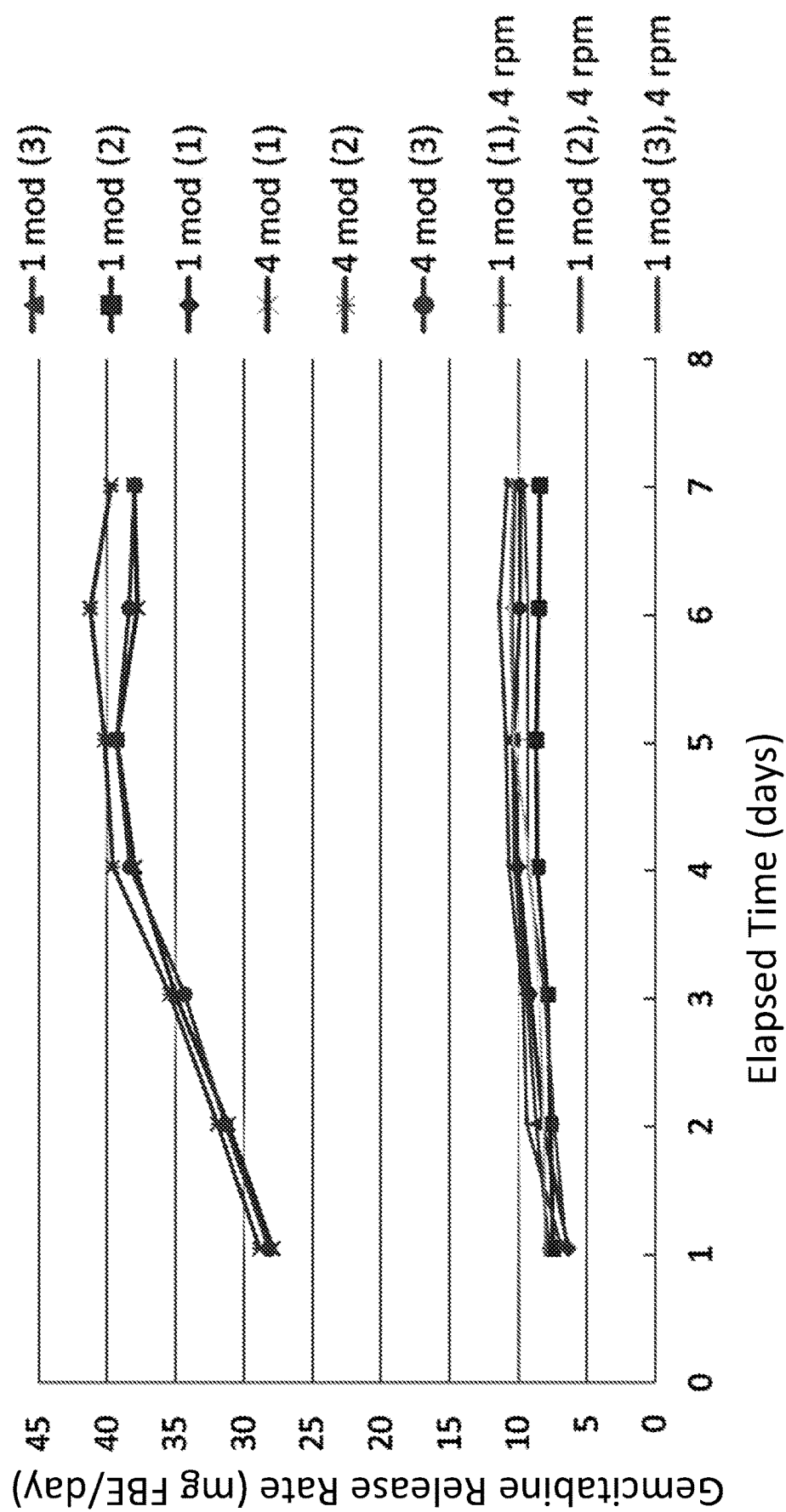
FIG. 28 is a graph showing the release rate of gemcitabine from static and rotated devices having drug permeable end wall disks, over time.
Figure 29:
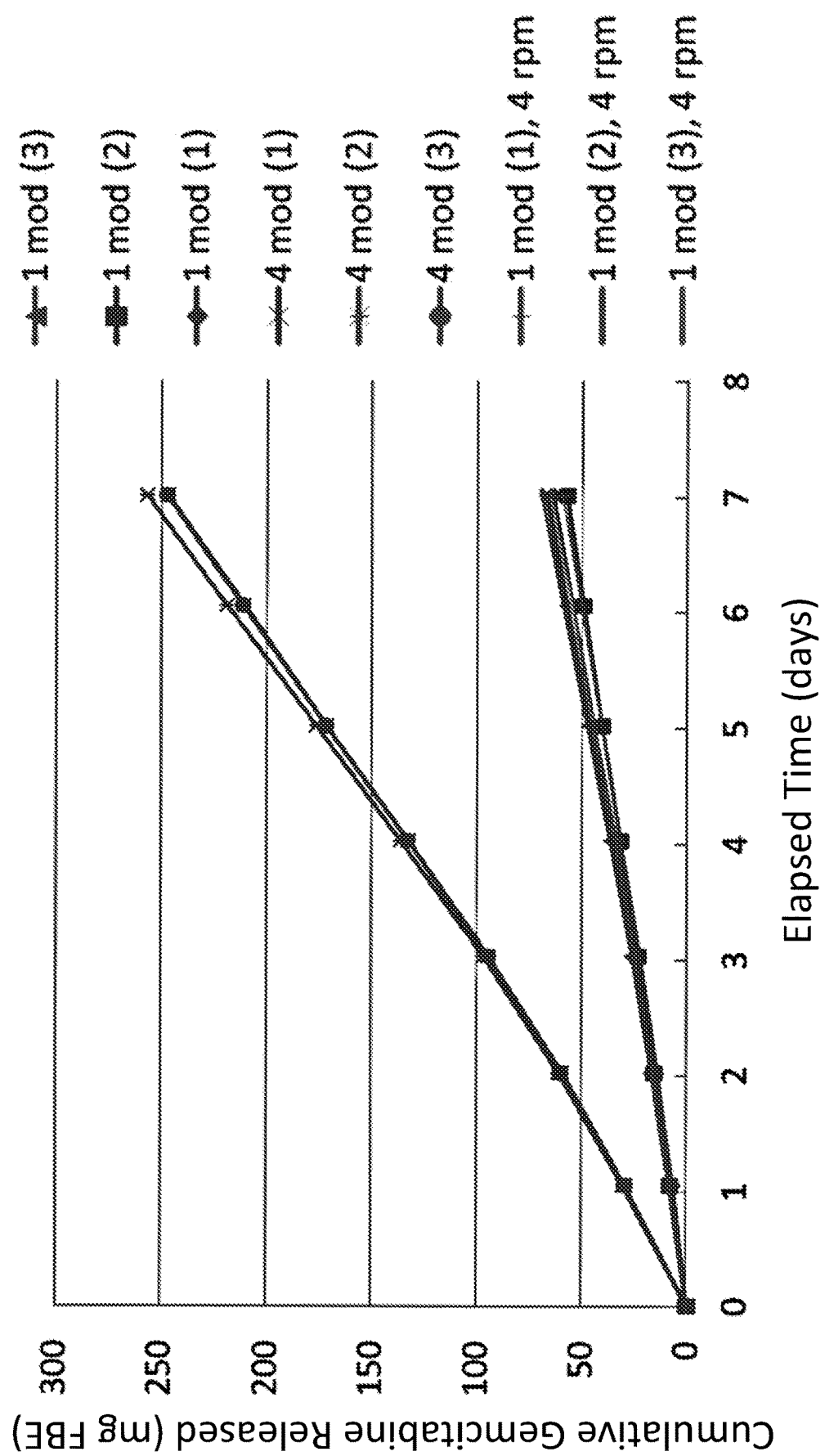
FIG. 29 is a graph showing the cumulative amount of gemcitabine released from static and rotated devices having drug permeable end wall disks, over time.
Figure 30:
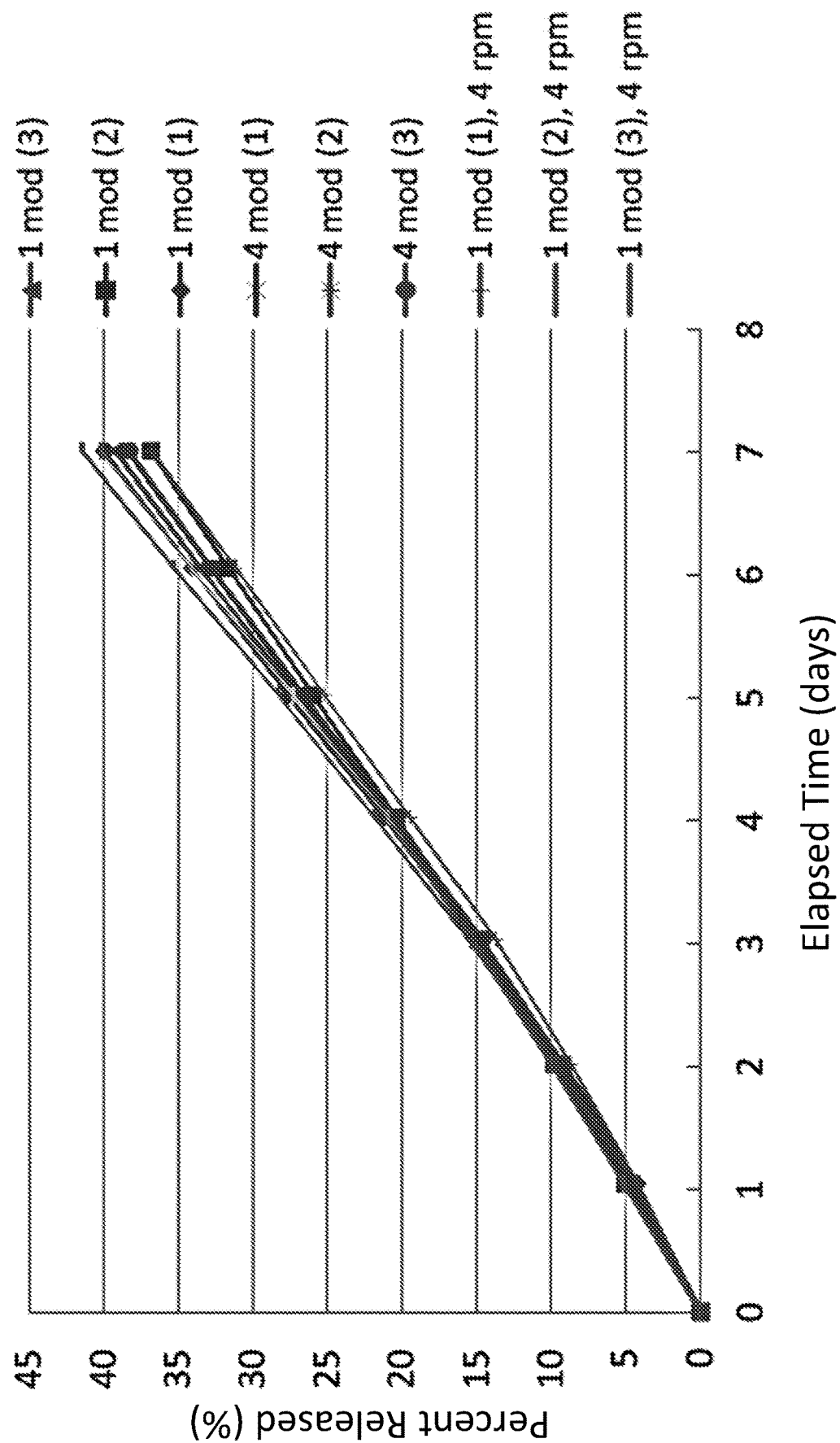
FIG. 30 is a graph showing the percent amount of gemcitabine released from static and rotated devices having drug permeable end wall disks, over time.

A silicone tube made of MED-4750 (Nusil) had dimensions of 2.64 mm ID and 0.20 mm wall thickness. Multiple gemcitabine HCl tablets with 2.6 mm OD were loaded into the silicone tube with a total gemcitabine HCl payload of approximately 97 mg. The device had a disk made of HP-93A-100 (Tecophilic™ Thermoplastic Polyurethanes) at one of the drug core and the other end was sealed by silicone adhesive. The dimensions of each disk were approximately 0.5 mm thickness and 3.0 mm OD. The OD (3.0 mm) of the disks was larger than the silicone tube ID (2.64 mm), and so the disks were frictionally fit in the silicone tube. In addition, there were polyimide washers located at both sides of the disk. The dimensions of the polyimide washers were 2.67 mm ID, 0.064 mm wall, and approximately 1-2 mm length. The inner washer was filled with a tablet so that the disk was initially in contact with the tablet. The layout of each device in the silicone tube was: Polyimide Outer Washer—Disk—Polyimide Inner Washer—Tablets—Sealed. Three devices were built and placed in deionized water at 37° C. for in vitro release experiment. Results are shown in FIG. 27. Each error bar shown below is standard deviation around the mean (n=3). Y-axis indicates gemcitabine release rate, and the unit is mg FBE (Free Base Equivalent) per day.

Example 5

There were three experimental groups tested: 1) one module device with the releasing jar being rotated in the rotator at 4 rpm ('Rotator'), 2) one module device without the jar rotated ('Static'), and 3) four module device without the jar rotated ('Static'). Each module is comprised of silicone tube made of MED-4750 (Nusil) with the dimensions of 2.64 mm ID and 0.20 mm wall thickness. Multiple gemcitabine HCl tablets with 2.6 mm OD were loaded into the silicone tube with each module having a total gemcitabine HCl payload of approximately 190 mg. The tablet formulation was 90% gemcitabine HCl, 5% PVP, 2.5% Neusilin, and 2.5% magnesium stearate. Each module had a disk made of HP-93A-100 (Tecophilic™ Thermoplastic Polyurethanes) at each end of the tablet drug core. The dimensions of each disk were approximately 0.5 mm thickness and 3.0 mm OD. The OD (3.0 mm) of the disks was larger than the silicone tube ID (2.64 mm), and so the disks were frictionally fit in the silicone tube. Each module has a silicone outer washer, made of MED-4780 (Nusil), located next to each disk with silicone adhesive (MED3-4213) applied around the washer, to stabilize the outward migration of the disk. The silicone outer washer had the dimensions of ID, OD, and the length of approximately 2.5 mm, 3.2 mm, and 2 mm, respectively. In addition, each module has a polyimide inner washer with 2.67 mm ID, 0.064 mm wall, and approximately 4 mm length. The inner washer was filled with a tablet so that the disk was initially in contact with the tablet. The layout of each module in the silicone tube was: Silicone Outer Washer—Disk—Polyimide Inner Washer—Tablets—Polyimide Inner Washer—Disk—Silicone Outer Washer.

Figure 31:
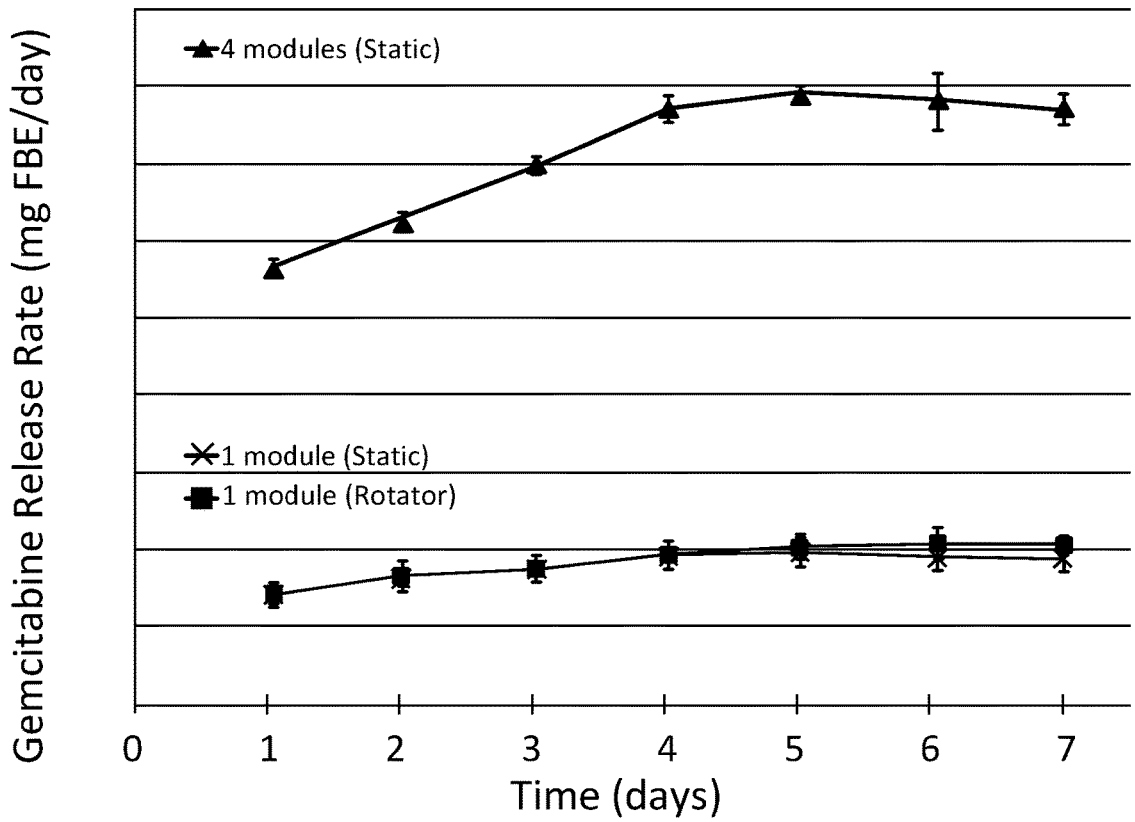
FIG. 31 is a graph showing the release rate of gemcitabine from static and rotated devices having drug permeable end wall disks, over time.

The cumulative and percent amounts of drug released, as well as the drug release rate are illustrated in FIGS. 28-31: one module device (Static), one module device (Rotator), and four module device (Static) (n=3 per each group). In FIG. 31, each error bar is standard deviation around the mean and Y-axis indicates gemcitabine release rate, and the unit is mg FBE (Free Base Equivalent) per day. Some error bars are smaller than symbols. There was no significant difference in gemcitabine release rate between release medium non-stirring group and stirring group (Static vs Rotator). Also, the gemcitabine release rate of the 4-module device was approximately four times higher than that of the 1-module device.

Example 6

Gemcitabine HCl was tested in a four module device. Each module was comprised of silicone tube made of MED-4750 (Nusil) with the dimensions of 2.64 mm ID and 0.20 mm wall thickness. Multiple tablets with 2.6 mm OD were loaded into the silicone tube. The tablet formulation was 90% gemcitabine HCl, 5% PVP, 2.5% Neusilin, and 2.5% magnesium stearate. Tablet mass loaded in four module device was approximately 800 mg. The silicone tube had an additional lumen with 0.51 mm ID and 0.20 mm wall as in FIG. 5A and nitinol retention frame was inserted into the lumen. Each module had a disk made of HP-93A-100 (Tecophilic™ Thermoplastic Polyurethanes) at both ends of the tablet drug core. The dimensions of each disk were approximately 0.5 mm thickness and 3.0 mm OD. The OD (3.0 mm) of the disk was larger than the silicone tube ID (2.64 mm), and so the disk was frictionally fit in the silicone tube.

Each module had inner and outer silicone washers, made of MED-4780 (Nusil), and located next to disks with silicone adhesive applied around the washers to fix it in the silicone tube. The silicone outer washer had the dimensions of ID, OD, and the length of approximately 2.5 mm, 3.2 mm, and 2 mm, respectively, and the silicone inner washer had the dimensions of ID, OD, and the length of approximately 1.58 mm, 2.77 mm, and 2 mm, respectively. The layout of each module in the silicone tube was: Silicone Outer Washer—Disk—Silicone Inner Washer—Tablets—Silicone Inner Washer—Disk—Silicone Outer Washer.

Figure 32:
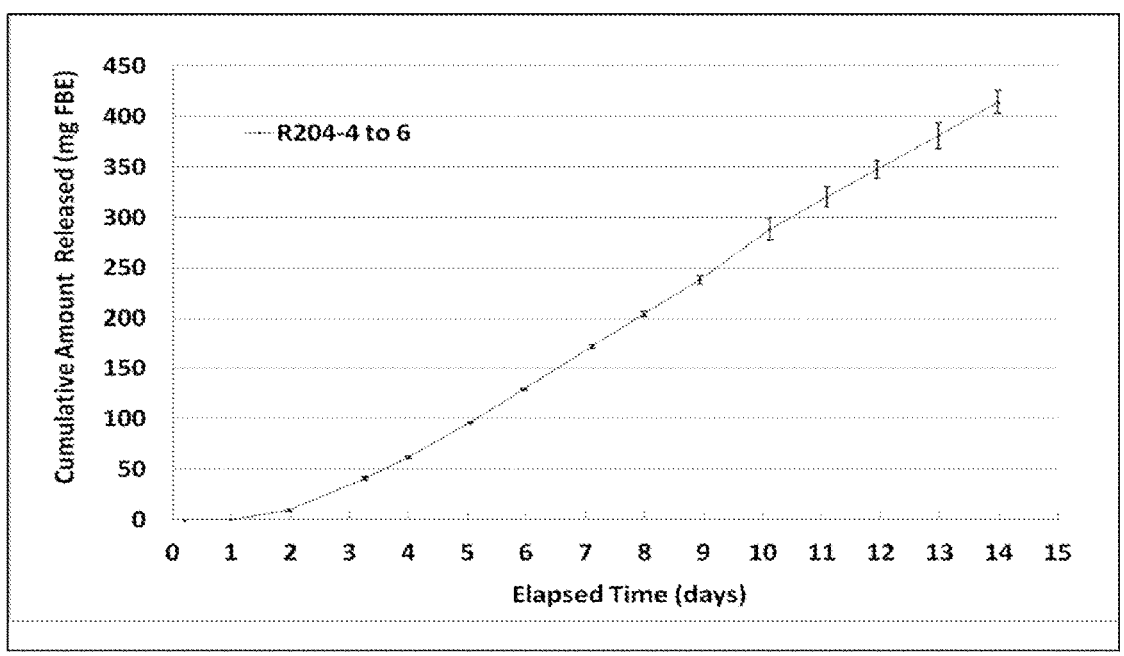
FIG. 32 is a graph showing the cumulative amount of gemcitabine released from a four module device having drug permeable end wall disks, over time.

In vitro release experiment with three units (R204-4 to 6) was performed at 37° C. The release medium was deionized water, and time point samples were collected over 14 days. The cumulative amount of drug released and the urine concentration of the samples were measured. The results are shown in FIG. 32. Each error bar is standard deviation around the mean (n=3). Some error bars are smaller than symbols.

The devices with the same design were tested in vivo with three Gottingen minipigs. Each device was inserted into the bladder of each animal through the urethra non-surgically by cystoscope. The urine concentration of gemcitabine plus 2',2'-difluoro-2'-deoxyuridine (dFdU), its terminal metabolite, was measured over 8 day period.

Figure 33:
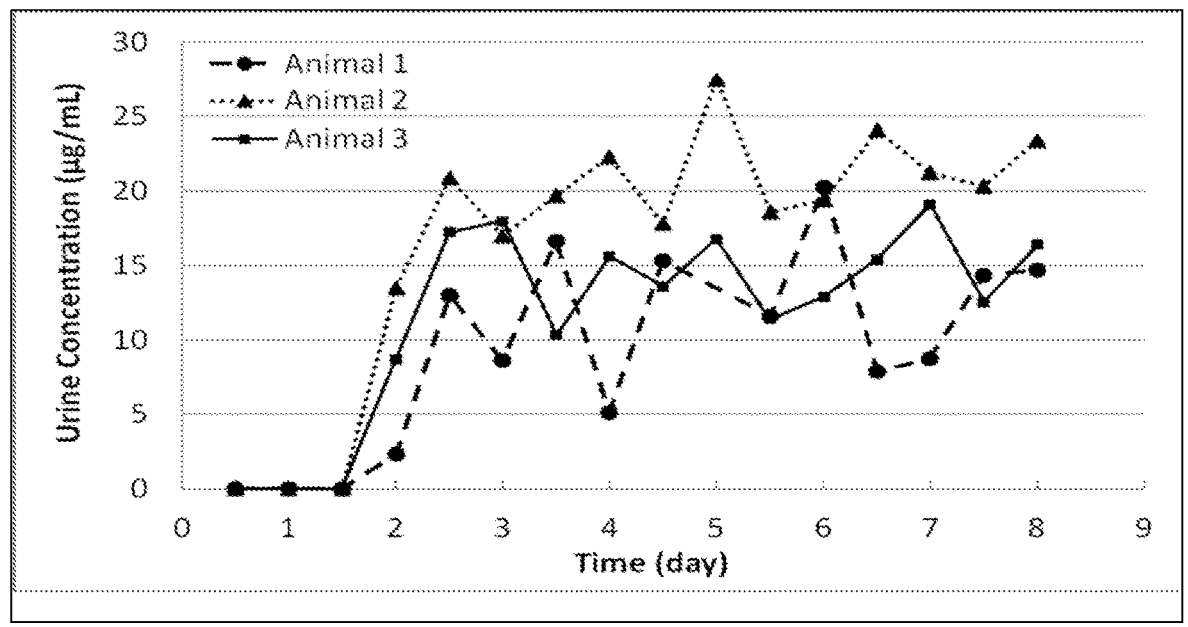
FIG. 33 is a graph showing the in vivo urine concentration of 2',2'-difluoro-2'-deoxyuridine (dFdU) at various times.

The results are shown in FIG. 33. After the 8 day study, each device was removed through the urethra non-surgically by cystoscope and forceps.

Example 7

Trospium chloride was tested in a single module device. A module was comprised of silicone tube made of MED-4750 (Nusil) with the dimensions of 2.64 mm ID and 0.20 mm wall thickness. Multiple trospium tablets with 2.6 mm OD were loaded into the silicone tube. The tablet formulation was trospium chloride without any excipient, and tablet mass loaded in each module was approximately 330 mg and the tablet core length was 5 cm long. The silicone tube had an additional lumen with 0.51 mm ID and 0.20 mm wall and nitinol retention frame was inserted into the lumen. Each module had a disk made of HP-93A-100 (Tecophilic™ Thermoplastic Polyurethanes) at one end of the tablet drug core while the other end was sealed by silicone adhesive. The dimensions of each disk were approximately 0.5 mm thickness and 3.0 mm OD. The OD (3.0 mm) of the disk was larger than the silicone tube ID (2.64 mm), and so the disk was frictionally fit in the silicone tube. Each module had a silicone washer, made of MED-4780 (Nusil), and located next to each disk with silicone adhesive applied around the washer. The silicone washer had the dimensions of ID, OD, and the length of approximately 2.5 mm, 3.2 mm, and 2 mm, respectively. The layout of each module in the silicone tube was: Silicone Washer—Disk—Tablets—Sealed.

Figure 34:
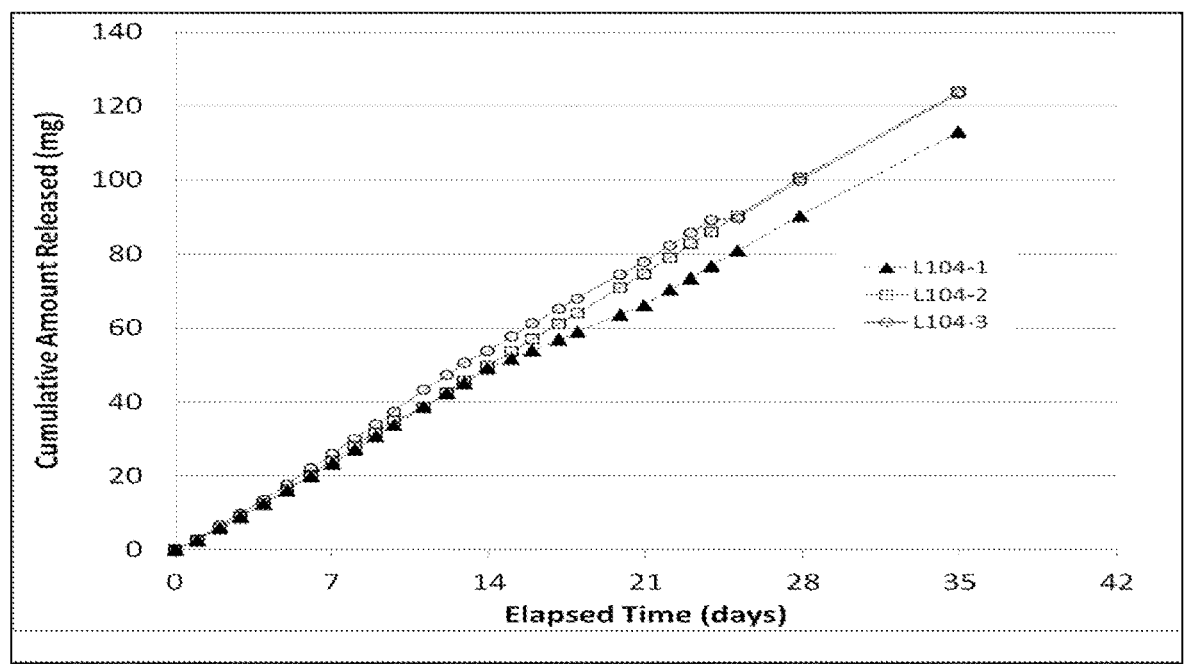
FIG. 34 is a graph showing the cumulative amount of tropsium chloride released from a single module device having a drug permeable end wall disk at one end, over time.

In vitro release experiment with three units was performed at 37° C. The release medium was 150 mM ammonium acetate buffer at pH 4.5 from Day 0 to Day 14. Then, from Day 14 to Day 21, each unit from L104-1 to L104-3 was moved to one of artificial urines with varying pHs and osmolalities: pH 8 and 1000 mmol/kg, pH 4 and 450 mmol/kg, and pH 8 and 450 mmol/kg, respectively. Then, from Day 21, the release medium was back to 150 mM ammonium acetate buffer at pH 4.5 for all units. The cumulative amount of drug released is shown in FIG. 34.

Example 8

Trospium chloride was tested in a single module device. A module was comprised of silicone tube made of MED-4750 (Nusil) with the dimensions of 2.64 mm ID and 0.20 mm wall thickness. Multiple trospium tablets with 2.6 mm OD were loaded into the silicone tube. The tablet formulation was trospium chloride (80.75% w/w), Plasdone K-29/32 (4.25% w/w), PROSOLV SMCC 50 (14.0% w/w), and magnesium stearate (1% w/w) and tablet mass loaded in each module was approximately 900 mg and the tablet core length was 14 cm long. The silicone tube had an additional lumen with 0.51 mm ID and 0.20 mm wall and nitinol retention frame was inserted into the lumen. Each module had a disk made of HP-93A-100 (Tecophilic™ Thermoplastic Polyurethanes) at one end of the tablet drug core while the other end was sealed by silicone adhesive. The dimensions of each disk were approximately 0.5 mm thickness and 3.0 mm OD. The OD (3.0 mm) of the disk was larger than the silicone tube ID (2.64 mm), and so the disk was frictionally fit in the silicone tube. Each module had a silicone washer, made of MED-4780 (Nusil), and located next to each disk with silicone adhesive applied around the washer to fix it. The silicone washer had the dimensions of ID, OD, and the length of approximately 2.5 mm, 3.2 mm, and 2 mm, respectively. The layout of each module in the silicone tube was: Silicone Washer—Disk—Tablets—Sealed.

Figure 35:
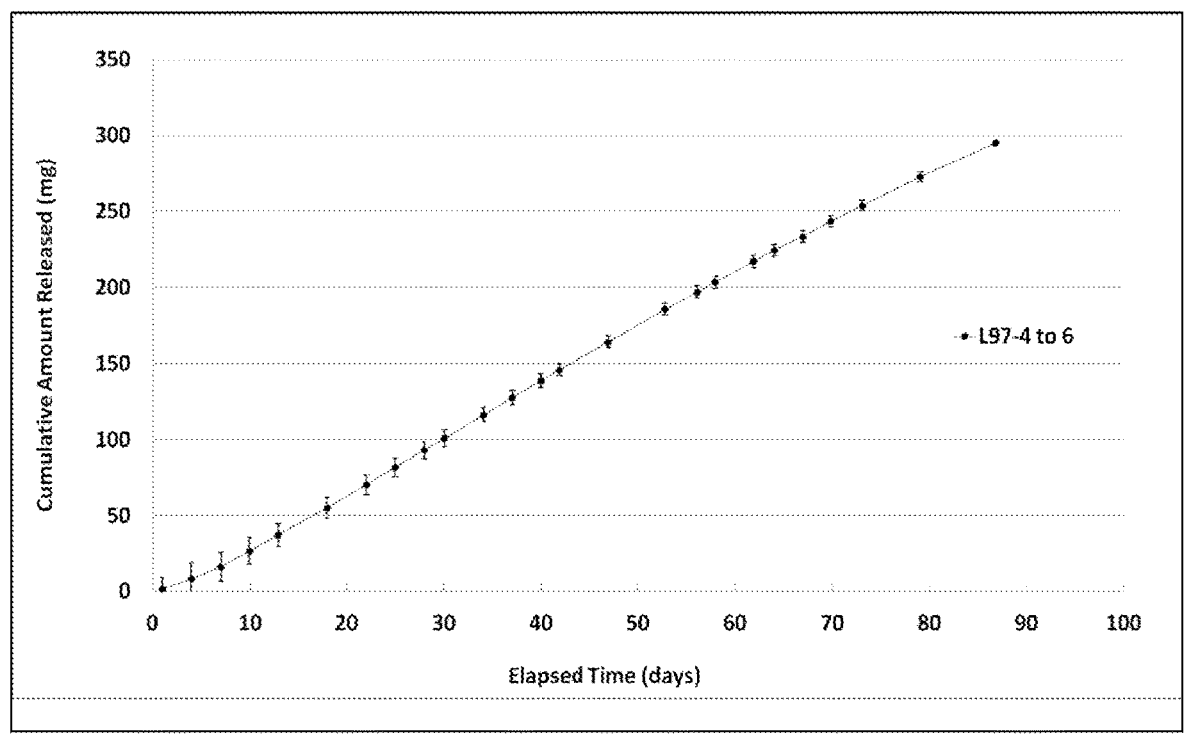
FIG. 35 is a graph showing the cumulative amount of tropsium chloride released from a single module device having a drug permeable end wall disk at one end, over time.

In vitro release experiment was performed at 37° C. and the release media was 150 mM ammonium acetate buffer at pH 4.5, and samples were collected over a 3 month period. The release media was changed to fresh one every two weeks. The results are given in FIG. 35. Each error bar is standard deviation around the mean (n=3). Some error bars are smaller than symbols.

Example 9

Lidocaine HCl was tested in a single module system. A module was comprised of silicone tube made of MED-4750 (Nusil) with the dimensions of 2.64 mm ID and 0.20 mm wall thickness. Multiple lidocaine HCl tablets with 2.64 mm OD were loaded into the silicone tube. The tablet formulation was lidocaine hydrochloride monohydrate (89.5% w/w), Plasdone K-29/32 (2.5% w/w), and Polyglykol 8000 PF (8.0% w/w), and tablet mass loaded in each module was approximately 320 mg and the tablet core length was 5 cm long. Each module had a disk made of HP-93A-100 (Tecophilic™ Thermoplastic Polyurethanes) at one end of the tablet drug core while the other end was sealed by silicone adhesive. The dimensions of each disk were approximately 0.5 mm thickness and 3.0 mm OD. The OD (3.0 mm) of the disk was larger than the silicone tube ID (2.64 mm), and so the disk was frictionally fit in the silicone tube. Each module had a silicone washer, made of MED-4780 (Nusil), and located next to each disk with silicone adhesive applied around the washer to fix it. The silicone washer had the dimensions of ID, OD, and the length of approximately 2.5 mm, 3.2 mm, and 2 mm, respectively. The layout of each module in the silicone tube was: Silicone Washer—Disk—Tablets—Sealed.

Figure 36:
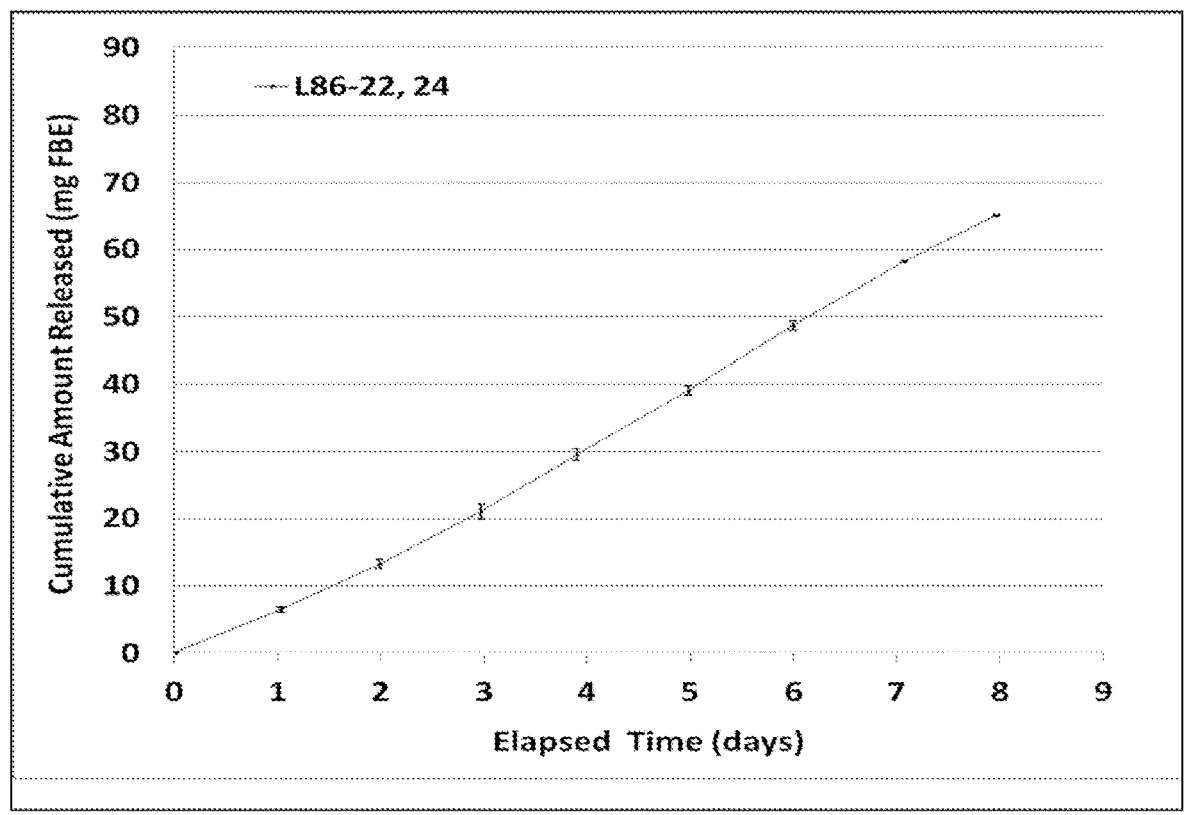
FIG. 36 is a graph showing the cumulative amount of lidocaine HCl released from a single module device having a drug permeable end wall disk at one end, over time.

In vitro release experiment was performed in deionized water at 37° C., and samples were collected over 8 day time period. The results are given in FIG. 36. Each error bar is standard deviation around the mean (n=2). Some error bars are smaller than symbols.

Example 10

Lidocaine HCl was tested in a side-hole device with the following layout: Inner silicone tube with two holes—Hydrophilic polymer band—Outer silicone sleeve with two holes. The inner silicone tube was made of MED-4750 (Nusil) with the dimensions of 1.52 mm ID, 0.2 mm wall, and contained the lidocaine tablets. The formulation of the tablets was lidocaine hydrochloride monohydrate (89.5% w/w), Plasdone K-29/32 (2.5% w/w), and Polyglykol 8000 PF (8.0% w/w). The tablet mass loaded was approximately 105 mg and the tablet core length was 5 cm. Two holes had approximately 1.2 mm diameter, and were created by manual punch in both inner silicone tube and outer silicone sleeve. Two punched holes were located opposite to each other. The hydrophilic polymer band was made of HP-93A-100 (Tecophilic™ Thermoplastic Polyurethanes) with 2.64 mm OD, 0.2 mm wall, and 1 cm length. Outer silicone sleeve had 3.05 mm ID, 0.2 mm wall, and 2 cm length. Silicone adhesive was applied between the inner silicone tube and outer silicone sleeve. The holes in the inner silicone tube and the outer silicone sleeve were aligned.

Figure 37:
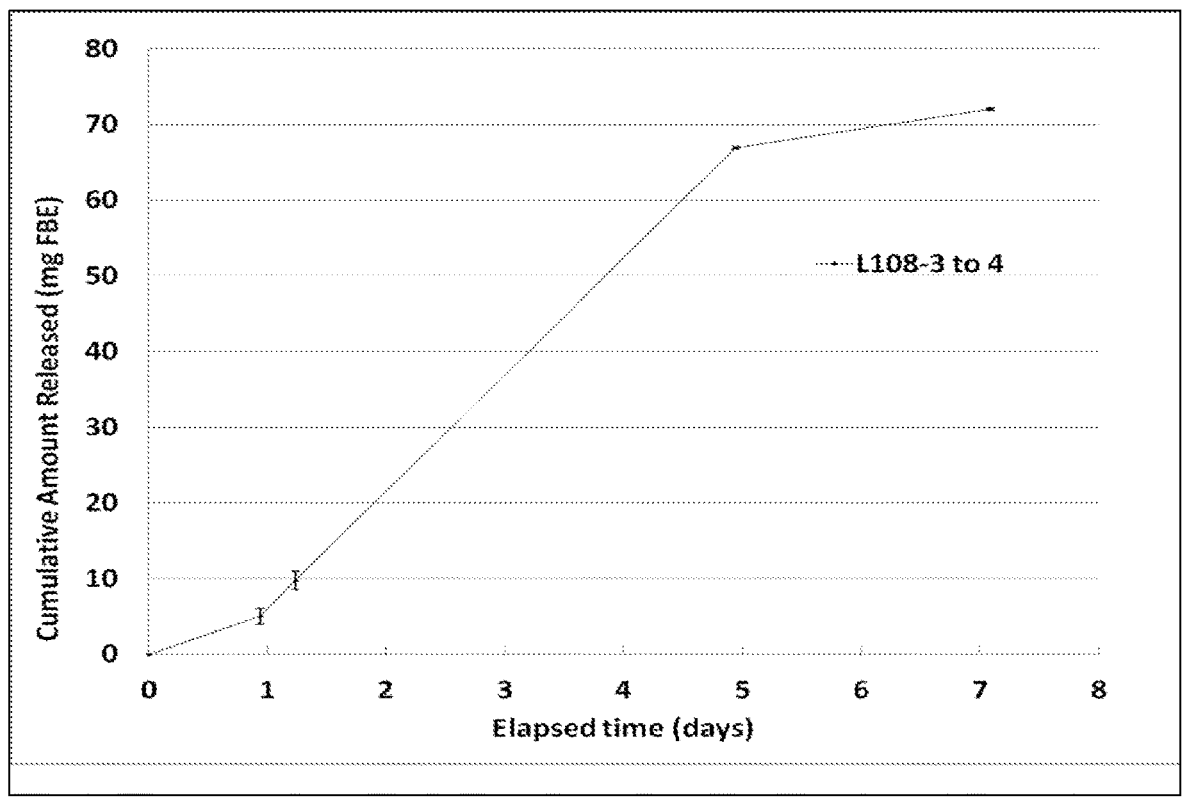
FIG. 37 is a graph showing the cumulative amount of lidocaine HCl released from a device having first and second wall structures that are adjacent one another and form a cylindrical tube, over time.

In vitro release experiment was performed in deionized water at 37° C., and samples were collected over 7 day period. The results are given in FIG. 37. Each error bar is standard deviation around the mean (n=2). Some error bars are smaller than symbols.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method of providing controlled release of drug to a patient, comprising:
    deploying into the patient, a drug delivery device comprising (i) a closed drug reservoir lumen bounded by a first wall structure constructed of a first material and by a second wall structure constructed of a second material, and (ii) a solid drug formulation which comprises a drug and is contained in the closed drug reservoir lumen,
    wherein water in the patient diffuses through the first and second wall structures into the closed drug reservoir lumen to contact and solubilize the drug formulation,
    wherein the drug is released from the drug delivery device, via diffusion through only the second wall structure, and
    wherein the first material and the second material are two different polymeric materials.

2. The method of claim 1, wherein the first wall structure and the second wall structure together form an elongated tube, with both the first and second wall structures extending the length of the elongated tube.

3. The method of claim 2, wherein the second material comprises a thermoplastic polyurethane.

4. The method of claim 1, wherein the first wall structure is a cylindrical tube and the second wall structure is an end wall at at least one end of the cylindrical tube.

5. The method of claim 1, wherein the first material comprises a water permeable material other than silicone.

6. The method of claim 1, wherein the second material comprises an elastomeric material.

7. The method of claim 6, wherein the elastomeric material comprises a thermoplastic polyurethane.

8. The method of claim 1, wherein deploying the drug delivery device into the patient comprises inserting, via a deployment instrument, the drug delivery device into the patient's bladder through the patient's urethra.

9. The method of claim 1, wherein deploying the drug delivery device into the patient comprises:
    releasing the drug delivery device into the patient whereby the drug delivery device elastically deforms from a relatively straightened shape to a curved retention shape effective to retain the drug delivery device within the patient.

10. The method of claim 9, wherein the drug delivery device is released into the patient's bladder.

11. The method of claim 1, wherein a rate of release of the drug from the drug delivery device is zero order over at least 36 hours.

12. The method of claim 1, wherein a rate of the release of the drug from the drug delivery device is zero order over at least 7 days.

13. The method of claim 1, wherein the solid drug formulation is in the form of a plurality of tablets.

14. The method of claim 1, wherein the first wall structure and the second wall structure are formed in a coextrusion process.

15. The method of claim 1, wherein the drug comprises lidocaine, gemcitabine, docetaxel, carboplatin, cisplatin, oxaliplatin, trospium, tolterodine, oxybutynin, or mitomycin C.

16. The method of claim 1, wherein the drug is a kinase inhibitor.

17. The method of claim 1, wherein the drug delivery device further comprises a retention frame lumen and a retention frame disposed therein.

18. The method of claim 17, wherein the retention frame comprises a nitinol wire.

19. The method of claim 1, wherein the drug comprises a fibroblast growth factor receptor-3 (FGFR3)-selective tyrosine kinase inhibitor.

20. The method of claim 1, wherein the second material comprises a polyether-based thermoplastic polyurethane.

21. The method of claim 1, wherein the second material has a Shore durometer value from about 70 A to about 65 D.

22. The method of claim 1, wherein the drug is released over a period of 90 days.

23. A method of providing controlled release of drug to a patient, comprising:
deploying a drug delivery device in the patient, the device comprising a closed drug reservoir lumen bounded by a first wall structure constructed of a first material and a second wall structure constructed of a second material different from the first material,
wherein a drug is released from the drug reservoir lumen via diffusion through the second material,
wherein the first wall structure is impermeable to the drug, and the second wall structure is permeable to the drug, and
wherein the first wall structure and the second wall structure are adjacent one another and together form an elongated tube, wherein the second wall structure forms a longitudinal strip extending along at least a portion of a length of the tube.

24. The method of claim 23, wherein deploying the drug delivery device in the patient comprises inserting the device into a body cavity or lumen of the patient via a deployment instrument.

25. The method of claim 24, wherein the body cavity is the bladder.

26. The method of claim 20, wherein deploying the drug delivery device in the patient comprises:
elastically deforming the drug delivery device into a relatively straightened shape; and
releasing the drug delivery device into the patient's body cavity such that the drug delivery device assumes a retention shape suited to retain the drug delivery device within the body cavity.

27. The method of claim 23, wherein a rate of release of the drug from the drug delivery device is zero order over at least 36 hours.

28. The method of claim 23, wherein a rate of the release of the drug from the drug delivery device is zero order over at least 7 days.

29. The method of claim 23, wherein releasing the drug further comprises solubilizing the drug with water imbibed through the second wall structure or both the first and second wall structures.

30. The method of claim 23, wherein the drug is in the form of one or more solid drug units.

31. The method of claim 23, wherein the drug comprises a fibroblast growth factor receptor-3 (FGFR3)-selective tyrosine kinase inhibitor.

32. The method of claim 23, wherein the first wall structure is formed of a water permeable material other than silicone.

33. The method of claim 23, wherein the second material has a Shore durometer value from about 70 A to about 65 D.

34. The method of claim 23, wherein the drug is released over a period of 90 days.

35. A method of providing controlled release of drug to a patient, comprising:
deploying into the patient, a drug delivery device comprising (a) an elongated tubular housing having two parallel lumen which extend between a first end and an opposing second end of the housing, wherein the two lumen are (i) a closed drug reservoir lumen bounded by a first wall structure constructed of a first material and a second wall structure constructed of a second material which comprises a thermoplastic polyurethane and is different from the first material, and (ii) a retention frame lumen; (b) a plurality of tablets comprising a kinase inhibitor, the plurality of tablets being contained in the drug reservoir lumen; and (c) a nitinol wire retention frame disposed in the retention frame lumen;
permitting water in the patient to diffuse through the first and second wall structures into the closed drug reservoir lumen to contact and solubilize the plurality of tablets comprising a kinase inhibitor; and
releasing the solubilized kinase inhibitor from the drug delivery device, via diffusion through only the second wall structure.

36. The method of claim 35, wherein the drug delivery device is deployed into the patient's bladder and assumes a coiled retention shape.

37. The method of claim 35, wherein the kinase inhibitor comprises a fibroblast growth factor receptor-3 (FGFR3)-selective tyrosine kinase inhibitor.

38. The method of claim 35, wherein the first wall structure is formed of a water permeable material other than silicone.

39. The method of claim 35, wherein the second material has a Shore durometer value from about 70 A to about 65 D.

40. The method of claim 35, wherein the solubilized kinase inhibitor is released from the drug delivery device over a period of 90 days.

41. The method of claim 35, wherein:
the kinase inhibitor comprises a fibroblast growth factor receptor-3 (FGFR3)-selective tyrosine kinase inhibitor and is released from the drug delivery device over a period of 90 days; and
the first wall structure is formed of a water permeable material other than silicone and the thermoplastic polyurethane of the second wall structure has a Shore durometer value from about 70 A to about 65 D.

42. An intravesical drug delivery device comprising:
an elongated tubular housing having two parallel lumen which extend between a first end and an opposing second end of the housing, wherein the two lumen are (i) a closed drug reservoir lumen bounded by a first wall structure constructed of a first material and a second wall structure constructed of a second material which comprises a thermoplastic polyurethane, and (ii) a retention frame lumen;

a plurality of tablets comprising a kinase inhibitor, the plurality of tablets being contained in the drug reservoir lumen; and a nitinol wire retention frame disposed in the retention frame lumen, wherein the first wall structure is impermeable to the kinase inhibitor, and the second wall structure is permeable to the kinase inhibitor, and wherein the first and second wall structures are water permeable, wherein the first and second wall structures extend the length of the tubular housing, with the second wall structure being in the form of a longitudinal strip extending the length of the elongated tubular housing, and wherein the device is configured to release the kinase inhibitor from the closed drug reservoir lumen by diffusion through the second material forming the second wall structure after water enters the drug reservoir lumen through at least one of the first and second wall structures and contacts the tablets.

43. The intravesical drug delivery device of claim 42, wherein the plurality of tablets is between 10 and 100 tablets.

44. The intravesical drug delivery device of claim 42, wherein the tablets are mini-tablets and each mini-tablet has end faces and a side face that is substantially cylindrical, with a diameter in the range of 1.0 mm to 3.2 mm and a length, extending along the side face, in the range of 1.7 mm to 4.8 mm.

45. The intravesical drug delivery device of claim 42, wherein the intravesical drug delivery device is configured to assume a coiled retention shape within a patient's bladder.

46. The device of claim 42, wherein the kinase inhibitor comprises a fibroblast growth factor receptor-3 (FGFR3)-selective tyrosine kinase inhibitor.

47. The device of claim 42, wherein the first wall structure is formed of a water permeable material other than silicone.

48. The device of claim 42, wherein the second material has a Shore durometer value from about 70 A to about 65 D.

49. The device of claim 42, wherein the solubilized kinase inhibitor is released from the drug delivery device over a period of 90 days.

* * * * *